(12) United States Patent
Chapman et al.

(10) Patent No.: US 7,432,338 B2
(45) Date of Patent: Oct. 7, 2008

(54) BRANCHED POLYMERS FROM ORGANOHYDROGENSILICON COMPOUNDS

(75) Inventors: Brian Douglas Chapman, Midland, MI (US); Loren Dean Durfee, Midland, MI (US); Timothy Paul Mitchell, Clio, MI (US); James Steven Tonge, Sanford, MI (US); Paul Cornelius Vandort, Sanford, MI (US)

(73) Assignee: Dow Corning Corporation, Midland, MI (US)

( * ) Notice: Subject to any disclaimer, the term of this patent is extended or adjusted under 35 U.S.C. 154(b) by 369 days.

(21) Appl. No.: 10/538,680

(22) PCT Filed: Dec. 17, 2003

(86) PCT No.: PCT/US03/40262

§ 371 (c)(1),
(2), (4) Date: Jun. 10, 2005

(87) PCT Pub. No.: WO2004/058858

PCT Pub. Date: Jul. 15, 2004

(65) Prior Publication Data

US 2006/0116500 A1 Jun. 1, 2006

Related U.S. Application Data

(60) Provisional application No. 60/435,902, filed on Dec. 20, 2002.

(51) Int. Cl.
C08G 77/12 (2006.01)
C08G 77/20 (2006.01)
C08G 77/04 (2006.01)

(52) U.S. Cl. .............................. 528/31; 528/32; 528/33

(58) Field of Classification Search .................. 528/31
See application file for complete search history.

(56) References Cited

U.S. PATENT DOCUMENTS

| | | | |
|---|---|---|---|
| 2,868,766 A | 1/1959 | Johannson | |
| 2,994,684 A | 8/1961 | Johannson | |
| 3,002,951 A | 10/1961 | Johannson | |
| 3,159,601 A | 12/1964 | Ashby | |
| 3,159,662 A | 12/1964 | Ashby | |
| 3,220,972 A | 11/1965 | Lamoreaux | |
| 3,296,291 A | 1/1967 | Chalk | |
| 3,372,178 A | 3/1968 | Wu | |
| 3,410,886 A | 11/1968 | Joy | |
| 3,419,593 A | 12/1968 | Willing | |
| 3,516,946 A | 6/1970 | Modic | |
| 3,814,730 A | 6/1974 | Karstedt | |
| 3,928,629 A | 12/1975 | Chandra et al. | |
| 3,989,668 A | 11/1976 | Lee et al. | |
| 3,996,195 A | 12/1976 | Sato et al. | |
| 4,245,079 A * | 1/1981 | Matsumoto et al. | 528/15 |
| 4,427,801 A | 1/1984 | Sweet | |
| 4,461,867 A | 7/1984 | Surprenant | |
| 4,525,400 A | 6/1985 | Surprenant | |
| 4,525,566 A | 6/1985 | Homan et al. | |
| 4,616,076 A | 10/1986 | Ona et al. | |
| 4,681,963 A | 7/1987 | Lewis | |
| 4,705,765 A | 11/1987 | Lewis | |
| 4,726,964 A | 2/1988 | Isobe et al. | |
| 4,849,491 A | 7/1989 | Ogawa et al. | |
| 4,900,779 A | 2/1990 | Leibfried | |
| 4,902,731 A | 2/1990 | Leibfried | |
| 5,036,117 A | 7/1991 | Chung et al. | |
| 5,097,054 A | 3/1992 | Yamamoto et al. | |
| 5,162,445 A | 11/1992 | Powers et al. | |
| 5,175,325 A | 12/1992 | Brown et al. | |
| 5,200,543 A | 4/1993 | Inomata et al. | |
| 5,290,841 A | 3/1994 | Enami et al. | |
| 5,344,906 A | 9/1994 | Westall | |
| 5,378,790 A | 1/1995 | Michalczyk et al. | |
| 5,412,055 A | 5/1995 | Loo | |
| 5,426,167 A | 6/1995 | Powers et al. | |
| 5,436,308 A | 7/1995 | Durfee et al. | |
| 5,525,696 A | 6/1996 | Herzig et al. | |

(Continued)

FOREIGN PATENT DOCUMENTS

EP 0259711 8/1987

(Continued)

OTHER PUBLICATIONS

U.S. Appl. No. 60/377,425, filed May, 1, 2002, Chapman.

(Continued)

*Primary Examiner*—Randy Gulakowski
*Assistant Examiner*—Robert Loewe
(74) *Attorney, Agent, or Firm*—Patricia M. Scaduto

(57) ABSTRACT

This invention relates to a method comprising (1) heating in the presence of a catalyst a mixture comprising (i) at least one organohydrogensilicon compound containing at least one silicon-bonded hydrogen atom per molecule or a reaction product obtained by mixing in the presence of a platinum group metal-containing catalyst at least one organohydrogensilicon compound containing at least one silicon-bonded hydrogen atom per molecule and at least one compound having at least one aliphatic unsaturation, (ii) at least one endblocker, and optionally (iii) at least one organosiloxane chosen from a hydrolyzate or a cyclosiloxane, so to cause polymerization of components (i), (ii), and optionally (iii) to form silicon-bonded hydrogen containing branched polymers.

20 Claims, No Drawings

U.S. PATENT DOCUMENTS

| | | | |
|---|---|---|---|
| 5,536,803 A * | 7/1996 | Fujiki et al. | .......... 528/15 |
| 5,545,831 A | 8/1996 | Kaiya et al. | |
| 5,545,837 A | 8/1996 | Kobayashi | |
| 5,548,051 A | 8/1996 | Michalczyk et al. | |
| 5,575,831 A | 11/1996 | Yamamura et al. | |
| 5,581,008 A | 12/1996 | Kobayashi | |
| 5,656,711 A | 8/1997 | Fukuda et al. | |
| 5,670,596 A | 9/1997 | Razzano et al. | |
| 5,691,435 A | 11/1997 | Herzig et al. | |
| 5,830,969 A | 11/1998 | Ahmed Jallouli et al. | |
| 5,883,215 A | 3/1999 | Bischoff et al. | |
| 5,985,462 A | 11/1999 | Herzig et al. | |
| 6,093,782 A | 7/2000 | Herzig et al. | |
| 6,127,502 A * | 10/2000 | Krahnke et al. | .......... 528/10 |
| 6,160,150 A | 12/2000 | Krahnke et al. | |
| 6,177,519 B1 | 1/2001 | Chung et al. | |
| 6,184,407 B1 | 2/2001 | Yoshitake et al. | |
| 6,235,832 B1 | 5/2001 | Deng et al. | |
| 6,252,100 B1 | 6/2001 | Herzig | |
| 6,300,452 B1 | 10/2001 | Jukarainen et al. | |
| 6,303,729 B1 | 10/2001 | Sato | |
| 6,313,255 B1 | 11/2001 | Rubinsztajn | |
| 6,353,075 B1 | 3/2002 | Hupfield et al. | |
| 6,528,584 B2 | 3/2003 | Kennedy et al. | |
| 6,605,734 B2 | 8/2003 | Roy et al. | |
| 2002/0099114 A1 * | 7/2002 | Nakayoshi et al. | .......... 523/209 |
| 2005/0256286 A1 | 11/2005 | Asch et al. | |
| 2006/0074212 A1 * | 4/2006 | Chapman et al. | .......... 528/15 |
| 2006/0111491 A1 * | 5/2006 | Asch et al. | .......... 524/261 |

FOREIGN PATENT DOCUMENTS

| | | |
|---|---|---|
| EP | 0464706 | 8/1995 |
| EP | 0416471 | 1/1999 |
| EP | 0600512 | 2/2000 |
| EP | 0979837 | 2/2000 |
| WO | WO 03/093349 | 11/2003 |
| WO | WO 03/093369 | 11/2003 |

OTHER PUBLICATIONS

Kurian et al., Novel Cyclosiloxane-Based Networks, Polymer Preprints 2003, 44(1), pp. 33-34.

Kurian et al., Novel Tricomponent Membranes Containing Poly(Ethylene Glycol)/Poly (Pentaamethylcyclopentasiloxane)/Poly (Dimethyulsiloxane) Domains, Journal of Polymer Science: Part A: Polymer Chemistry, vol. 40, 3093-3102 (2002).

Backer, M., et al.: Si Chemical Shift Tensors of Silyl Silicate Cages, Solid State Nuclear Magnetic Resonance, Netherlands, vol. 9, No. 2-4, Dec. 1997, pp. 241-255.

Koyava N. A., et al.: Synthesis of Organocyclosiloxanes with a Predetermined Arrangement of Functional Groups on the Silicon Atoms, Journal of General Chemistry of the USSR, vol. 50, No. 8, 1980, pp. 1461-1465.

Sokolov, N. N., et al.: Organocyclosiloxanes I. Methylchlorocyclsosiloxanes, Journal of General Chemistry of the USSR, vol. 26, 1956, pp. 1061-1063.

Sokolov, N. N., et al.: Organocyclosiloxanes II. Methylchlorocyclsosiloxanes, Journal of General Chemistry of the USSR, vol. 26, 1956, pp. 2545-2547.

Sakiyama, M., et al.: The Selective Halogenation of Methylhydropolysiloxanes: Syntheses of Methylhalopolysiloxanes and Their Derivatives, Bulletin of the Chemical Society of Japan, vol. 38, No. 12, 1965, pp. 2182-2186.

Andrianov, K. A., et al.: Substitution Reactions in Organocyclosiloxanes Containing Functional Groups Attached to the Silicon Atom, Chemistry of Heterocyclic Compounds, vol. 8, 1972, pp. 1068-1070.

Andrianov, K. A. et al.: Heterofunctional Condensation of Chlorosilanes with Tetra- and Hexaphenylsiloxanediols, Chemistry of Heterocyclic Compounds, vol. 8, 1972, pp. 810-812.

Kurian et al., Synthesis And Characterization of Novel Amphiphilic Block Copolymers Di-, Tri, Multi-, and Star Blocks of PEG and PIB, Journal of Polymer Science: Part A: Polymer Chemistry, vol. 38, 3200-3209 (2000).

Kurian et al. Novel Tricontinuous Hydrophilic-Lipophilic-Oxyphilic Membranes: Synthesis and Characterization, Journal of Polymer Science: Part A: Polymer Chemistry, vol. 40, 1209-1217 (2002).

* cited by examiner

BRANCHED POLYMERS FROM ORGANOHYDROGENSILICON COMPOUNDS

CROSS REFERENCE TO RELATED APPLICATIONS

This application is a U.S. national stage filing under 35 U.S.C. §371 of PCT Application No. PCT/US2003/040262 filed on Dec. 17, 2003, currently pending, which claims the benefit of U.S. Provisional Patent Application No. 60/43 5,902 filed Dec. 20, 2002 under 35 U.S.C. §119 (e). PCT Application No. PCT/US2003/040262 and U.S. Provisional Patent Application No. 60/435,902 are hereby incorporated by reference.

DESCRIPTION

This invention relates to a method comprising (1) heating in the presence of a catalyst a mixture comprising (i) at least one organohydrogensilicon compound containing at least one silicon-bonded hydrogen atom per molecule or a reaction product obtained by mixing in the presence of a platinum group metal-containing catalyst at least one organohydrogensilicon compound containing at least one silicon-bonded hydrogen atom per molecule and at least one compound having at least one aliphatic unsaturation, (ii) at least one endblocker, and optionally (iii) at least one organosiloxane chosen from a hydrolyzate or a cyclosiloxane, so to cause polymerization of components (i), (ii), and optionally (iii) to form silicon-bonded hydrogen containing branched polymers.

Polymers containing branching and methods for making them are known. However, due to the starting materials generally used, it is difficult to independently control the many parameters of polymer architecture oftentimes resulting in polymer species having undesired end-group functionality. In addition, methodologies reported in the literature for synthesis of branched polymers using components containing silicon-alkylene linkages result in products which exhibit low viscosity, low Dp (degree of polymerization), low branching content or high viscosity, high Dp, high branching content. One object of the present invention is to use a cyclic branched intermediate without end-groups so to independently control properties such as branching, end-group level, end-group identity, and Dp. Another object is to produce low viscosity, high Dp, highly branched silicon-bonded hydrogen containing polymers.

This invention relates to a method comprising (1) heating in the presence of a catalyst a mixture comprising (i) at least one organohydrogensilicon compound containing at least one silicon-bonded hydrogen atom per molecule or a reaction product obtained by mixing in the presence of a platinum group metal-containing catalyst at least one organohydrogensilicon compound containing at least one silicon-bonded hydrogen atom per molecule and at least one compound having at least one aliphatic unsaturation (ii) at least one endblocker, and optionally (iii) at least one organosiloxane chosen from a hydrolyzate or a cyclosiloxane, so to cause polymerization of components (i), (ii), and optionally (iii) to form silicon-bonded hydrogen containing branched polymers. These Si-H containing branched polymers may be used as is or may be hydrosilylated prior to use.

The present invention is a method comprising (1) heating in the presence of a catalyst, a mixture comprising (i) at least one organohydrogensilicon compound containing at least one silicon-bonded hydrogen atom per molecule or a reaction product obtained by mixing in the presence of a platinum group metal-containing catalyst at least one organohydrogensilicon compound containing at least one silicon-bonded hydrogen atom per molecule and at least one compound having at least one aliphatic unsaturation where in each case the organohydrogensilicon compound is described by formula (I)

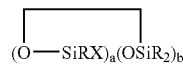

where each R is independently selected from a hydrogen atom and a monovalent hydrocarbon group comprising 1 to 20 carbon atoms which is free from aliphatic unsaturation, a is an integer from 1 to 18, b is an integer from 1 to 19, a+b is an integer from 3 to 20, each X is an independently selected functional group selected from a halogen atom, an ether group, an alkoxy group, an alkoxyether group, an acyl group, or a silyl group, or a $-Z-R^4$ group, where each Z is independently selected from an oxygen and a divalent hydrocarbon group comprising 2 to 20 carbon atoms, each $R^4$ group is independently selected from $-BR_uY_{2-u}$, $-SiR_vY_{3-v}$, or a group described by formula (II):

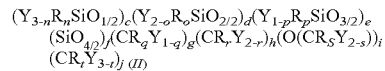

where B refers to boron, each R is as described above, the sum of c+d+e+f+g+h+i+j is at least 2, n is an integer from 0 to 3, o is an integer from 0 to 2, p is an integer from 0 to 1, q is an integer from 0 to 1, r is an integer from 0 to 2, s is an integer from 0 to 2, t is an integer from 0 to 3, u is an integer from 0 to 2, v is an integer from 0 to 3, each Y is an independently selected functional group selected from a halogen atom, an ether group, an alkoxy group, an alkoxyether group, an acyl group, or a silyl group, or a Z-G group, where Z is as described above, each G is a cyclosiloxane described by formula (III):

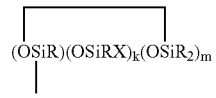

where R and X are as described above, k is an integer from 0 to 18, m is an integer from 0 to 18, k+m is an integer from 2 to 20, provided in formula (II) that one of the Y groups is replaced by the Z group bonding the $R^4$ group to the cyclosiloxane of formula (I), and provided further at least one X group of Formula (I) is a $-Z-R^4$ group;

(ii) at least one endblocker described by formula (IV) $R'_3SiO(MeR'SiO)_zSiR'_3$, where z ranges from 0 to 150 and each R' is independently chosen from hydrogen, alkyl, aryl, alkenyl, dienyl or functional alkyls where the functionality may be fluoro, fluoroether, polyether, ether, aryl, silyl, siloxy, carboxy, glycosidyl or acrylate, and optionally (iii) at least one organosiloxane chosen from a hydrolyzate described by formula (V) $HO(MeR'SiO)_{y'}H$ and a cyclosiloxane described by formula (VI) $(MeR'SiO)_y$ where y is an integer from 3 to 30, y' is an integer from 1 to 500, and each R' is as described above;

provided if component (i) is a reaction product and it does not contain any silicon-bonded hydrogen bonds then at least one R' of either component (ii) or (iii) is hydrogen, so to cause polymerization of components (i), (ii), and optionally (iii) to form silicon-bonded hydrogen containing branched polymers.

Component (i) of the present method comprises at least one organohydrogensilicon compound containing at least one silicon-bonded hydrogen atom per molecule as described by formula (I) above or a reaction product obtained by mixing in the presence of a platinum group metal-containing catalyst at least one organohydrogensilicon compound containing at least one silicon-bonded hydrogen atom per molecule as described above and at least one compound having at least one aliphatic unsaturation. It is preferred that component (i) is a reaction product as described above.

With respect to the organohydrogensilicon compounds used as component (i) or used to make the reaction product used as component (i) for the present method, each R group described in formulas (I), (II), and (III) is independently selected from a hydrogen atom and a monovalent hydrocarbon group comprising 1 to 20 carbon atoms free from aliphatic unsaturation. Each monovalent hydrocarbon group of R can be linear, branched or cyclic. Each monovalent hydrocarbon group of R can be unsubstituted or substituted with halogen atoms. The monovalent hydrocarbon group of R can be exemplified by alkyl groups such as methyl, ethyl, propyl, butyl, hexyl, octyl, 3,3,3-trifluoropropyl, nonafluorobutylethyl, chloromethyl, and decyl, cycloaliphatic groups such as cyclohexyl, aryl groups such as phenyl, tolyl, and xylyl, chorophenyl, and aralkyl groups such as benzyl, styryl and alpha-methylstyryl. It is preferred that each R group is independently selected from hydrogen atoms, alkyl groups comprising 1 to 8 carbon atoms, or aryl groups comprising 6 to 9 carbon atoms. It is most preferred that each R group is independently selected from hydrogen, methyl, alpha-methylstyryl, 3,3,3-trifluoropropyl and nonafluorobutylethyl. Each R can be identical or different, as desired.

In formula (I), a is an integer from 1 to 18, b is an integer from 1 to 19, preferably from 2 to 19, and a+b is an integer from 3 to 20.

In formulas (I) and (III) of the organohydrogensilicon compound, each X is an independently selected functional group selected from a halogen atom, an ether group, an alkoxy group, an alkoxyether group, an acyl group, or a silyl group, or a -Z-$R^4$ group.

The functional groups represented by X are selected from halogen atoms, ether groups, alkoxy groups, alkoxyether groups, acyl groups, or silyl groups. Examples of useful halo groups include chloro, fluoro, and bromo. Examples of useful alkoxy groups include methoxy, ethoxy, and isopropoxy. Examples of useful alkoxyether groups include ethylene glycol monopropyl ether and ethylene glycol monohexyl ether. Other useful functional groups are derived by hydrosilylation of the vinyl group from methylvinylether, methylvinylketone, vinylacetate, vinylbenzoate, vinylacrylate, vinylstearate, vinyldecanoate, vinylmethacrylate, trimethylvinylsilane, triethylvinylsilane, vinyltrimethoxysilane, vinyltriacetoxysilane, phenylvinylether, phenylvinylketone, and allyl aldehyde with an Si-H from the siloxane precursor to formulas (I) or (III).

When X is a functional group, it is preferred that each X is independently selected from chloro, methoxy, or isopropoxy. Each X of formulas (I) and (III) may also comprise a -Z-$R^4$ group. It is more preferred that X is a -Z-$R^4$ group.

Each Z is independently selected from oxygen and divalent hydrocarbon groups comprising 2 to 20 carbon atoms. Examples of the divalent hydrocarbon group comprising 2 to 20 carbon atoms represented by Z include alkylene radicals such as methylene, ethylene, methylmethylene, propylene, isopropylene, butylene, pentylene, hexylene, and octadecylene; alkenylene radicals such as vinylene, allylene, butenylene, and hexenylene, arylene radicals such as phenylene and xylylene; aralkylene radicals as benzylene; and alkarylene radicals such as tolylene. Preferably, Z is a divalent hydrocarbon group comprising 2 to 18 carbon atoms. It is more preferred for Z to be an alkylene group, with an alkylene group comprising 2 to 8 carbon atoms being most preferred.

Each $R^4$ group is selected from -$BR_uY_{2-u}$, -$SiR_vY_{3-v}$, or a group described by formula (II): $(Y_{3-n}R_nSiO_{1/2})_c(Y_{2-o}R_o$-$SiO_{2/2})_d(Y_{1-p}R_pSiO_{3/2})_e(SiO_{4/2})_f(CR_qY_{1-q})_g(CR_rY_{2-r})_h(O(CR_sY_{2-s}))_i(CR_tY_{3-t})_j$, where R, Y, c, d, e, f, g, h, i, j, n, o, p, q, r, s, t, u, v are as described above, provided in formula (II) that one of the Y groups is replaced by the Z group bonding the $R^4$ group to the cyclosiloxane of formula (I).

In formula (II) of the organohydrogensilicon compound, the sum of c+d+e+f+g+h+i+j is at least 2, preferably from 2 to 5300, more preferably from 2 to 1000. Preferably, subscript c is an integer from 0 to 50, with 2 to 15 being more preferred, and 2 to 10 being most preferred. Preferably, subscript d is an integer from 0 to 5000, with 0 to 1000 being more preferred, and 1 to 50 being most preferred. Preferably, subscript e is an integer from 0 to 48, with 0 to 13 being more preferred, and 0 to 8 being most preferred. Preferably, subscript f is an integer from 0 to 24, with 0 to 6 being more preferred, and 0 to 4 being most preferred. Preferably, subscript g is an integer from 0 to 50, with 0 to 20 being more preferred, and 0 to 10 being most preferred. Preferably, subscript h is an integer from 0 to 50, with 0 to 20 being more preferred, and 0 to 10 being most preferred. Preferably, subscript i is an integer from 0 to 50, with 0 to 20 being more preferred, and 0 to 10 being most preferred. Preferably, subscript j is an integer from 0 to 50, with 0 to 15 being more preferred, and 0 to 10 being most preferred.

In formula (II) of the organohydrogensilicon compound, n is an integer from 0 to 3, preferably from 2 to 3; o is an integer from 0 to 2, preferably from 1 to 2; p is an integer from 0 to 1, preferably 1; q is an integer from 0 to 1, preferably 1; r is an integer from 0 to 2, preferably from 1 to 2; s is an integer from 0 to 2, preferably from 1 to 2; and t is an integer from 0 to 3, preferably from 2 to 3. Notwithstanding the above, since the $R^4$ group as described by formula (II) is connected to the cyclosiloxane described by formula (I) via a Z group, one of the Y groups present in the $R^4$ group described by formula (II) will be replaced by a Z group.

In addition to a group described by formula (II), each $R^4$ group is independently selected from -$BR_uY_{2-u}$, and -$SiR_vY_{3-v}$ where B refers to boron, u is an integer from 0 to 2, preferably from 1 to 2 and v is an integer from 0 to 3, preferably from 2 to 3. Examples of these $R^4$ groups are derived from borane or silanes, such as for example, trivinylborane, diallyldimethylsilane, divinyldimethylsilane and vinyltrimethylsilane.

Each Y of $R^4$ is an independently selected functional group selected from a halogen atom, an ether group, an alkoxy group, an alkoxyether group, an acyl group, or a silyl group, or a -Z-G group. The functional groups are exemplified as described above for X. The Z group is also as described above.

Each G is a cyclosiloxane described by formula (III):

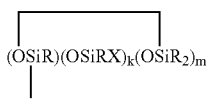

where R and X are as described above, k is an integer from 0 to 18, m is an integer from 0 to 18, and k+m is an integer from 2 to 20.

In formula (III) of the organohydrogensilicon compound, each k is an integer from 0 to 18, preferably from 1 to 3.

In formula (III) of the organohydrogensilicon compound, each m is an integer from 0 to 18, preferably from 1 to 10, most preferably from 2 to 4.

The sum of k+m is an integer from 2 to 20, preferably from 2 to 6, most preferably from 2 to 5.

The Y group of formula (II) is preferably a -Z-G group. Although it is not required for there to be any -Z-G groups in the organohydrogensilicon compounds useful in the present method, it is preferred that on average the organohydrogensilicon molecules contain at least 1-Z-G group with at least 2-Z-G groups being more preferred.

The $R^4$ group described by formula (II) can be linear, cyclic, branched or resinous. The $R^4$ group described by formula (II) can be a siloxane material where the polymer chain units contain only siloxane units, or it can be a mixture of siloxane units with hydrocarbon units or oxyhydrocarbon units, where oxyhydrocarbon refers to a hydrocarbon group which also includes at least one oxygen atom, or it can be a hydrocarbon material where the polymer chain units contain only hydrocarbon units or oxyhydrocarbon units. It is preferred that the $R^4$ group comprises hydrocarbon units, oxyhydrocarbon units, or siloxane units, with siloxane units being more preferred.

Examples of preferred $R^4$ groups described by formula (II) include —$CH_2CH_2$—, —$CH_2CH_2CH_2CH_2$—, —$O(CH_2CH_2O)_{z'}$—, where $z'$=1-100, —$O(CH_2\ CH_2\ CH_2O)_{z''}$—, where $z''$=1-100 and siloxane groups described by —$R_2SiO(R_2SiO)_dSiR_2$-Z-G, —$R_2SiOSiR_3$, —$R_2SiOSiR_2$—Y, —$RSi(OSiR_3)_2$, where d is an integer from 1 to 50 and Z, G, and R are as described above. More preferred $R^4$ groups are the siloxane groups as described above when R is methyl, and d is an average of 8.

With respect to the organohydrogensilicon compounds useful in the present method, it is preferred that at least one X group of Formula (I) is a -Z-$R^4$ group.

It is also preferred that the organohydrogensilicon compounds have a viscosity from to 50,000 mPa.s, more preferred from 10 to 10,000 mPa.s and most preferred from 25 to 2,000 mPa.s.

The organohydrogensilicon compounds used to make as component (i) or used to make the reaction product used as component (i) for the present method contain at least one silicon-bonded hydrogen atom per molecule. Preferably, the organohydrogensilicon compounds contain at least 2 silicon-bonded hydrogen atoms per molecule. It is most preferred that the organohydrogensilicon compounds contain at least 3 silicon-bonded hydrogen atoms per molecule. The organohydrogensilicon compounds may be a single species or a mixture of different species.

Examples of the types of organohydrogensilicon compounds included in the scope of the present invention are as follows where Me is methyl, d (which equals $d_1+d_2$) is as described above, and x can range from 1 to 100; preferably 1 to 20.

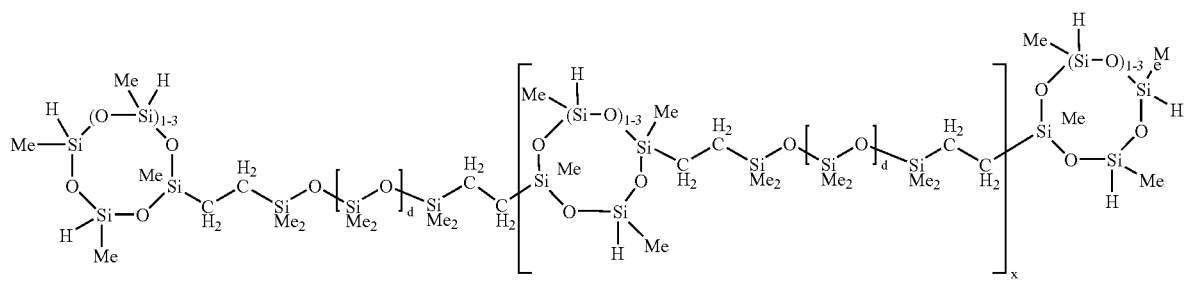

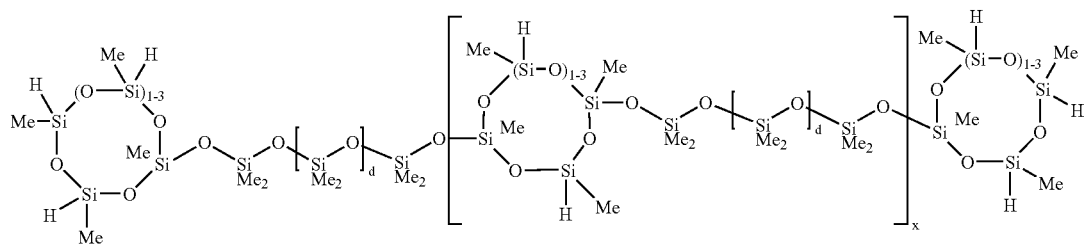

-continued
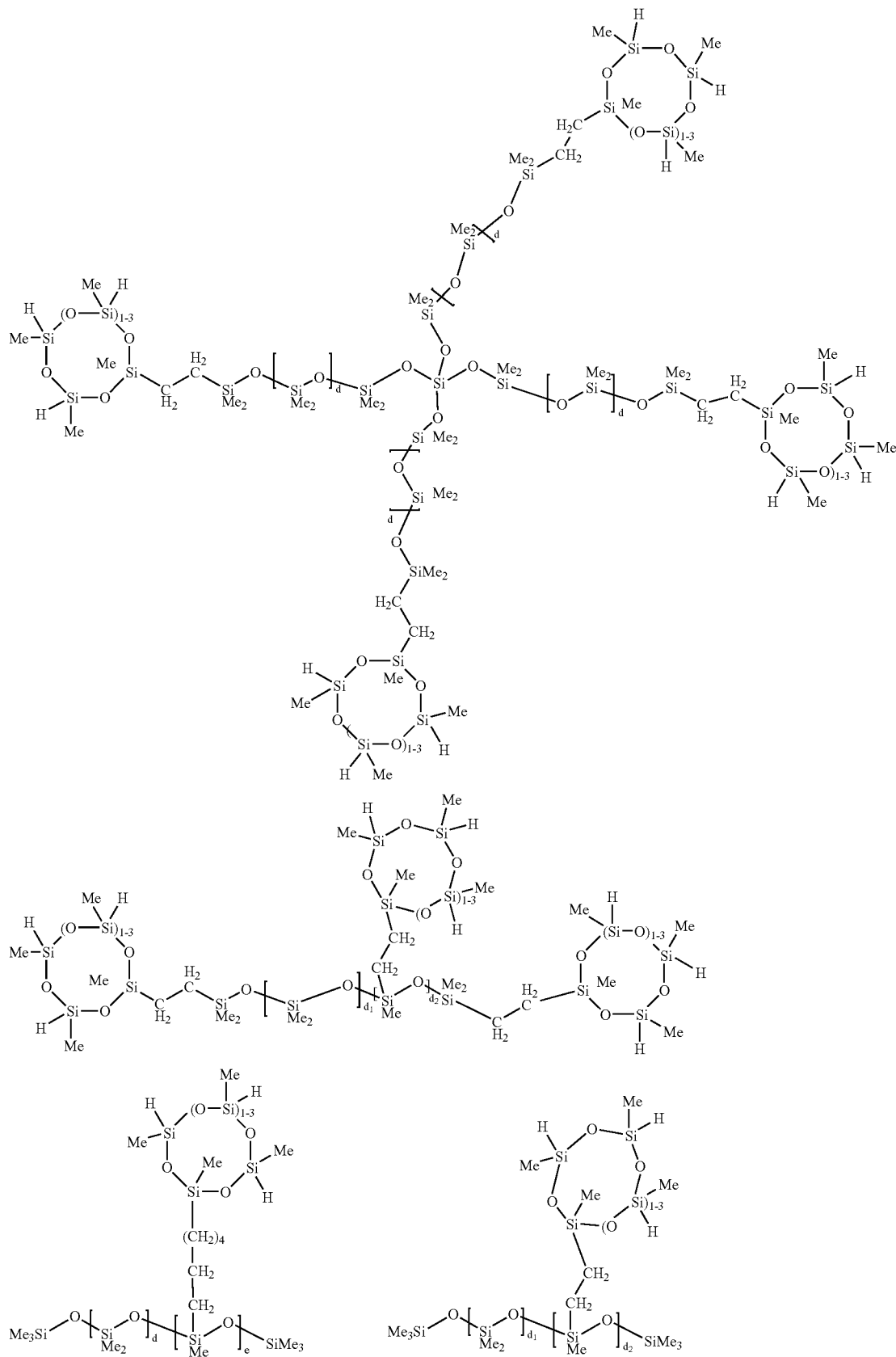

-continued
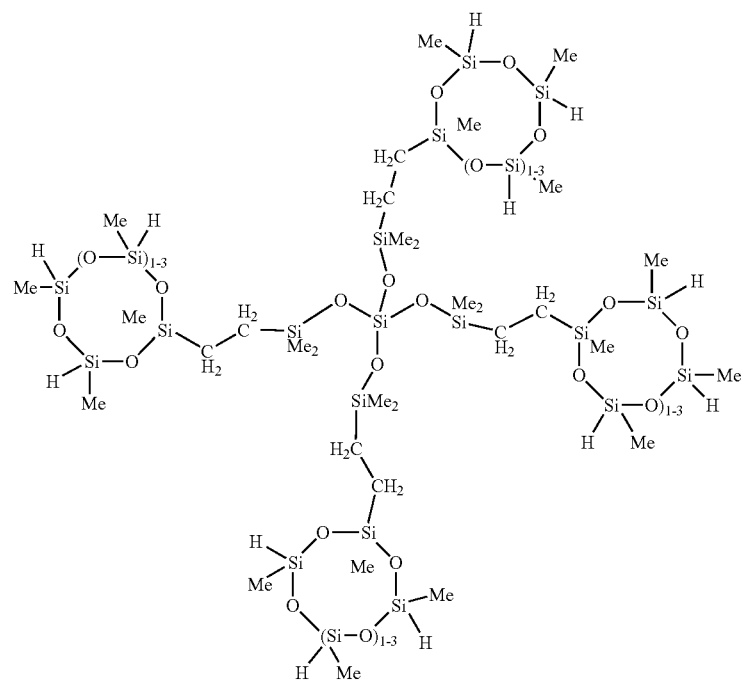
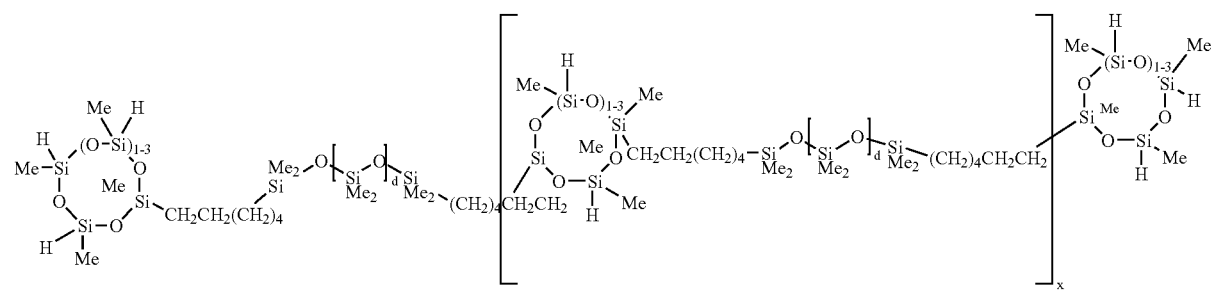
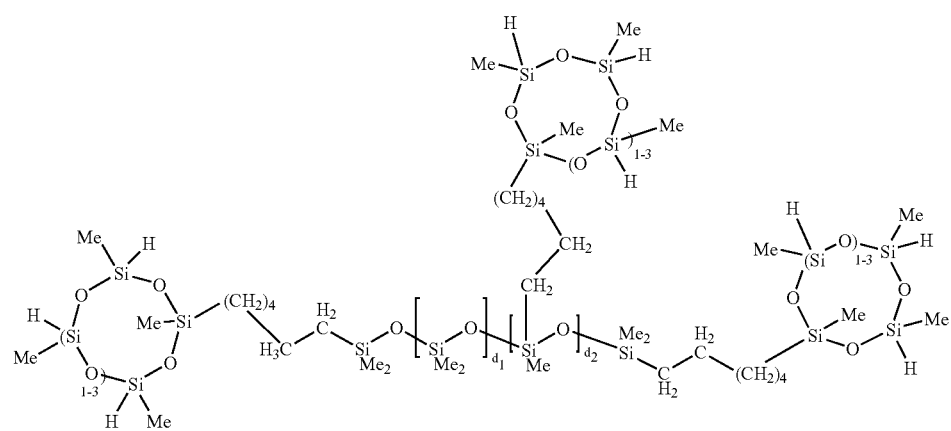

-continued

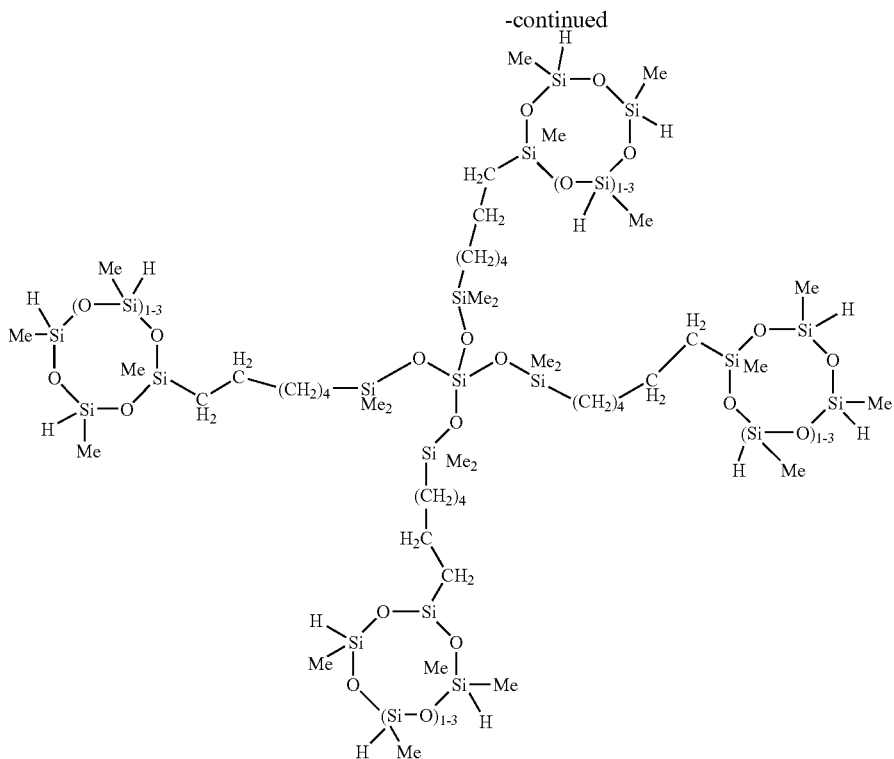

The most preferred organohydrogensilicon compounds described by formula (I) are as follows where Me is methyl, d is an average of 8, and x is an integer from 0 to 15:

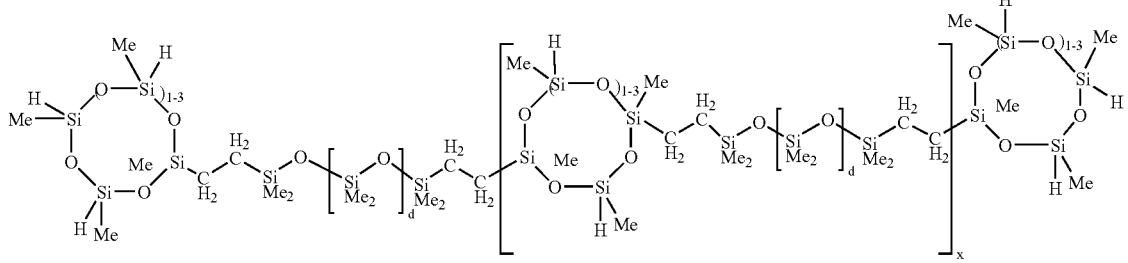

The organohydrogensilicon compounds can be made in a straightforward manner, for example via a platinum catalyzed coupling of (A) organohydrogen cyclosiloxanes having at least 2 Si-H groups per molecule with (B) a reactant containing at least one aliphatic unsaturation, hydroxy functionality or a mixture of both at temperatures from 20 to 150° C. Generally, the ratio of Si-H to aliphatic unsaturation or Si-H to hydroxy functionality useful to prepare the organohydrogensilicon compounds useful in the present method is at least 2.5:1.

Various organohydrogensilicon compounds and methods of making the organohydrogensilicon compounds are also described in U.S. patent application Ser. No. 60/377,425 and PCT application Ser. No. US03/13203 which are hereby incorporated by reference. The desired product is a function not only of the reactants but also of the reaction stoichiometry.

The reaction can be conducted by premixing the reactants followed by catalysis or by using one of the reactants as a controlling reagent. Since it is desired to react aliphatically unsaturated groups or hydroxy groups randomly with as many Si-H containing molecules as possible, the reaction may be conducted by premixing component (A) and (B) as described above, and then catalyzing the premix; by precatalyzing component (A) followed by controlled introduction of component (B), by precatalyzing component (B) and then adding this premix to component (A), or by something in between these three extremes.

The compounds having at least one aliphatic unsaturation used to make the reaction product of component (i) can be linear, branched, resinous or cyclic and can be monomers or polymers (including copolymers, terpolymers etc.) provided there is at least one aliphatic unsaturation. The compounds containing aliphatic unsaturation have alkenyl (also described as olefinic) unsaturation or alkynyl (also described as acetylenic) unsaturation. These compounds are well-known in the art of hydrosilylation and are disclosed in such patents as U.S. Pat. No. 3,159,662 (Ashby), U.S. Pat. No. 3,220,972 (Lamoreaux)), and U.S. Pat. No. 3,410,886 (Joy), which disclosures of said compounds are incorporated herein by reference. In instances where these unsaturated compounds contain elements other than carbon and hydrogen, it is preferred that these elements be oxygen, nitrogen, silicon, a halogen, or a combination thereof.

The aliphatically unsaturated compound can contain one or more carbon-carbon multiple bonds. Representative examples of the aliphatically unsaturated hydrocarbons which can be employed include mono-olefins, for example, ethene (ethylene), propene, 1-pentene and 1-hexene, diolefins, for example, divinylbenzene, butadiene, 1,5-hexadiene and 1-buten-3-yne, cycloolefins, for example, cyclohexene and cycloheptene, and monoalkynes, for example, acetylene, propyne and 1-hexyne.

Oxygen-containing aliphatically unsaturated compounds can also be used, especially where the unsaturation is ethylenic, such methylvinyl ether, divinylether, phenylvinyl ether, monoallyl ether of ethylene glycol, allyl aldehyde, methylvinyl ketone, phenylvinyl ketone, acrylic acid, methacrylic acid, methyl acrylate, allyl acrylate, methyl methacrylate, allyl methacrylate, vinylacetic acid, vinyl acetate, and linolenic acid.

Heterocyclic compounds containing aliphatic unsaturation in the ring, such as dihydrofuran, and dihydropyran, are also suitable to react with the organohydrogensilicon compounds.

Halogenated derivatives of the previously mentioned aliphatically unsaturated compounds can be employed, including acyl chlorides as well as compounds containing a halogen substituent on a carbon atom other than a carbonyl carbon atom. Such halogen-containing compounds include, for example, vinyl chloride, and the vinylchlorophenyl esters.

Unsaturated compounds containing nitrogen substituents such as acrylonitrile, N-vinylpyrrolidone, alkyl cyanide, and nitroethylene, are also useful.

Other compounds useful for making component (i) include polymers (including copolymers, terpolymers etc.) of the various compounds described above provided there is at least one aliphatic unsaturation. Examples include polymers derived from oxyhydrocarbon repeating units such as poly (alkyleneglycol) polymers with one or two allyloxy or vinyloxy end-cap groups. Common examples are polymers and copolymers of ethylene glycol and/or propylene glycol.

Another useful type of compound which can be reacted with the organohydrogensilicon compounds is that containing silicon, such as those compounds commonly referred to as organosilicon compounds. The useful organosilicon compounds have at least one aliphatically unsaturated group attached to silicon per molecule. The aliphatically unsaturated organosilicon compounds include silanes, siloxanes, silazanes, as well as monomeric or polymeric materials containing silicon atoms joined together by hydrocarbyl groups such as alkylene or polyalkylene groups or arylene groups. The silicon-modified organic compounds useful in making component (i) include organic monomers or polymers such as described above having at least one silicon atom attached as a silane or a siloxane segment. The silicon-containing units can contain aliphatic unsaturation and can be attached at the terminal and/or pendant positions on the organic polymer chain or as a copolymer.

Silanes useful in the present invention can be described by formula (VII)

where each $R^1$ is an independently selected monovalent hydrocarbon radical comprising 1 to 20 carbon atoms free from aliphatic unsaturation, each Q is independently selected from a monovalent hydrocarbon group comprising 2 to 20 carbon atoms having at least one aliphatic unsaturation, a monovalent oxyhydrocarbon group comprising 2 to 20 carbon atoms having at least one aliphatic unsaturation, a halogen atom, an alkoxy group, or an acyl group, provided at least one Q group has at least one aliphatic unsaturation, and w is an integer from 0 to 3.

Examples of silanes include vinyltrimethylsilane, vinyldimethylchlorosilane, vinylmethyldichlorosilane, hexenyldimethylchlorosilane, and hexenylmethyldichlorosilane, and vinyltriacetoxysilane.

Examples of silane-modified organic polymers are silylated polymers derived from olefins, isomonoolefin, dienes, ethylene or propylene oxides, and vinyl aromatic monomers having 2 to 20 carbon atoms such as the silane-grafted copolymers of isomonoolefin and vinyl aromatic monomer as discussed in U.S. Pat. Nos. 6,177,519 and 5,426,167. Other representative silicon-modified organic polymers are illustrated by, but not limited to alkenylsiloxy-functional polymers such as vinylsiloxy-, allylsiloxy-, and hexenylsiloxy-organic polymers and siloxane-organic block copolymers.

Examples of organosilicon polymers and silicon-modified organic polymers include trimethylsiloxy-terminated polydimethylsiloxane-polymethylvinylsiloxane copolymers, trimethylsiloxy-terminated polydimethylsiloxane-polymethylhexenylsiloxane copolymers, trimethylsiloxy-terminated polymethylvinylsiloxane polymers, trimethylsiloxy-terminated polymethylhexenylsiloxane polymers, polydimethylsiloxane polymers with one or two vinyl or hexenyl terminations, poly(dimethylsiloxane-monomethylsilsesquioxane) polymers with one or multiple vinyl or hexenyl terminations, trimethylsiloxy terminated poly(dimethylsiloxane-vinylmethylsiloxane-methylsilsesquioxane) polymers, trimethylsiloxy terminated poly(dimethylsiloxane-hexenylmethylsiloxane-methylsilsesquioxane) polymers, poly (dimethylsiloxane-silicate) copolymers with one or multiple vinyl or hexenyl terminations, trimethylsiloxy terminated poly(dimethylsiloxane-vinylmethylsiloxane-silicate) copolymers and trimethylsiloxy terminated poly(dimethylsiloxane-hexenylmethylsiloxane-silicate) copolymers, poly (dimethylsiloxane-hydrocarbyl) copolymers with one or two vinyl or hexenyl terminations, poly(dimethylsiloxane—polyoxyalkylene) block copolymers with one or two vinyl or hexenyl termination, polyisobutylene and polydimethylsiloxane-polyisobutylene block copolymers with one or two alkenyl terminations.

To form the reaction product of component (i), at least one compound having at least one aliphatic unsaturation is reacted with the organohydrogensilicon compounds described above. Therefore, one compound having at least one aliphatic saturation or a mixture of different compounds may be used. In addition, the compound can also have one or more aliphatic unsaturations. In preferred embodiments, the compound comprises at least one compound having at least one aliphatic unsaturation. Most preferred is when only a single type of compound having one aliphatic unsaturation is used.

The compounds comprising at least one aliphatic unsaturation may be a single species or a mixture of different species. They are commercially available or may be made by methods known in the art.

The platinum group metal-containing catalyst useful for catalyzing the hydrosilylation reaction between the organohydrogensilicon compound and the compound having at least one aliphatic unsaturation to make the reaction product of component (i) comprises any catalyst typically employed for hydrosilylation reactions. By platinum group it is meant ruthenium, rhodium, palladium, osmium, iridium and platinum and complexes thereof. Platinum group metal-containing catalysts useful in preparing the compositions of the present invention are the platinum complexes prepared as described by Willing, U.S. Pat. No. 3,419,593, and Brown et al, U.S. Pat. No. 5,175,325, each of which is hereby incorporated by reference to show such complexes and their preparation. Other examples of useful platinum group metal-containing catalysts can be found in Lee et al., U.S. Pat. No. 3,989,668; Chang et al., U.S. Pat. No. 5,036,117; Ashby, U.S. Pat. No. 3,159,601; Lamoreaux, U.S. Pat. No. 3,220,972; Chalk et al., U.S. Pat. No. 3,296,291; Modic, U.S. Pat. No. 3,516,946; Karstedt, U.S. Pat. No. 3,814,730; and Chandra et al., U.S. Pat. No. 3,928,629 all of which are hereby incorporated by reference to show useful platinum group metal-containing catalysts and methods for their preparation. The platinum-containing catalyst can be platinum metal, platinum metal deposited on a carrier such as silica gel or powdered charcoal, or a compound or complex of a platinum group metal. Preferred platinum-containing catalysts include chloroplatinic acid, either in hexahydrate form or anhydrous form, and or a platinum-containing catalyst which is obtained by a method comprising reacting chloroplatinic acid with an aliphatically unsaturated organosilicon compound such as divinyltetramethyldisiloxane, or alkene-platinum-silyl complexes as described in U.S. patent application Ser. No. 10/017,229, filed Dec. 7, 2001, such as $(COD)Pt(SiMeCl_2)_2$, where COD is 1,5-cyclooctadiene and Me is methyl. These alkene-platinum-silyl complexes may be prepared, for example by mixing 0.015 mole $(COD)PtCl_2$ with 0.045 mole COD and 0.0612 moles $HMeSiCl_2$.

The appropriate amount of the platinum group metal-containing catalyst will depend upon the particular catalyst used. The platinum catalyst should be present in an amount sufficient to provide at least 2 parts per million (ppm), preferably 5 to 200 ppm of platinum based on total weight percent solids (all non-solvent ingredients) in the composition. It is highly preferred that the platinum is present in an amount sufficient to provide 5 to 150 weight ppm of platinum on the same basis. The catalyst may be added as a single species or as a mixture of two or more different species. Adding the catalyst as a single species is preferred. The platinum group metal-containing catalyst is commercially available or may be made by methods known in the art.

The reaction product useful as component (i) of the present method is prepared by mixing organohydrogensilicon compounds as described above with at least one compound having at least one aliphatic unsaturation as described above in the presence of a platinum group-containing catalyst. The ratio of aliphatic unsaturation to Si-H can be from 100 to 0.01, preferably from 1.5 to 1. It is most preferred that a sufficient ratio of aliphatic unsaturation to Si-H be added so that all silicon-bonded hydrogen bonds on the organohydrogensilicon compound be reacted. These materials can be mixed together using any suitable mixing means, such as a spatula, a drum roller, a mechanical stirrer, a three roll mill, a sigma blade mixer, a bread dough mixer, and a two roll mill. The temperature of the reaction is not strictly specified, but generally falls within the range of about 20° to 150° C. The length of reaction time is also not critical, and is generally determined by the addition rate of controlling reagent. Optionally, the reaction can be run using common solvents such as toluene, xylene, methylisobutylketone, and heptane.

Prior to starting the present method, it may be desirable to remove any residual platinum from the hydrosilylation reaction used either for preparation of the organohydrogensilicon compounds and/or the reaction product of component (i) in order to reduce the opportunity for hydrolysis or self-condensation of any Si-H bonds via platinum catalysis. Any standard method of deactivation/removal is acceptable including addition of inhibition by organic molecules, Lewis base binding agents containing N, S, or P groups, filtration through complexation media such as carbon black or a combination of these techniques Component (ii) of the present method comprises at least one endblocker described by formula (IV) $R'_3SiO(MeR'SiO)_z SiR'_3$ where z ranges from 0 to 150, and R' is independently chosen from hydrogen, alkyl, aryl, alkenyl, dienyl or functional alkyls where the functionality may be fluoro, fluoroether, polyether, ether, aryl, silyl, siloxy, carboxy, glycosidyl or acrylate.

Examples of alkyl groups of R' include groups having the formula $C_nH_{2n+1}$, where n is an integer from 1 to 30; cycloaliphatic groups such as cyclohexyl, multivalent alkyl bridges such as derived from trivinylcyclohexane or doubly reacted dienes. Example of alkenyl groups include vinyl and higher alkenyls such as 5-hexenyl, 6-heptenyl, 7-octenyl, 8-nonenyl, 9-decenyl, 10-undecenyl and cyclohexenylethyl. Examples of dienyl substitution include 4,7-octadienyl, 5,8-nonadienyl, 5,9-decadienyl, 6,11-dodecadienyl, and 4,8-nonadienyl. Examples of aryl groups include phenyl, tolyl and xylyl. Examples of functional alkyls include fluoroalkyls such as chloromethyl, trifluoropropyl, and hexafluorobutylethyl; fluoroalkylethers such as $—CH_2CH_2CH_2O(CH_2)_2(CF_2)_nCF_3$ where n is an integer from 1 to 10; polyethers such as polyalkyleneglycol monoallyl ethers, polyalkyleneglycol monovinylether, polyalkyleneglycol allylmethyl ethers, polyalkyleneglycol vinylmethylether, polyalkyleneglycol allyl acetate and polyalkyleneglycol vinylacetate; aralkyls such as benzyl, styryl, and alpha-methylstyryl; alkylsilyls such as methyltrimethylsilane and hexyltrimethylsilane; alkylsiloxanes such as ethylpentamethyldisiloxane or hexylpentamethyldisiloxane; acrylates such as allylmethacrylate; ethers such as vinylphenylether; acetates such as vinylacetate; glycosidyls such as allylglucosides with the general formula of allyl-$C_5H_5(OR)_4$. It is preferred that each R' is independently chosen from H, alkyl, aryl, fluoroalkyl, fluoroalkylether, alkenyl or polyalkenylglycols. It is more preferred that each R' is independently chosen from H, alkyl, fluoroalkyl, or alkenyl. Each R' can be identical or different, as desired.

Subscript z is an integer from 0 to 150. Preferably, z is an integer from 0 to 50. More preferably, z is an integer from 0 to 8.

Component (ii) may be added in amounts from 0.5 to 5000 parts by weight per 100 parts by weight of component (i), preferably 3 to 1000 parts by weight on the same basis and most preferably from 10 to 150 parts by weight on the same basis. Component (ii) may be a single species or a mixture of different species. Component (ii) is commercially available or may be made by methods known in the art.

Optional component (iii) of the present method comprises at least one organosiloxane chosen from a hydrolyzate described by formula (V) $HO(MeR'SiO)_yH$ or a cyclosiloxane described by formula (VI) (MeR'SiO)$_y$, where y is an integer from 3 to 30, y' is an integer from 1 to 500 and each R' is independently chosen from hydrogen, alkyl, aryl, alkenyl, dienyl or functional alkyls where the functionality may be fluoro, fluoroether, polyether, ether, aryl, silyl, siloxy, carboxy, glycosidyl or acrylate. This component can be added when additional silicone is needed to build molecular weight or increase the degree of polymerization.

Each R' group of formulas (V) and (VI) is independently chosen from hydrogen, alkyl, aryl, alkenyl, dienyl or functional alkyls where the functionality may be fluoro, fluoroether, polyether, ether, aryl, silyl, siloxy, carboxy, glycosidyl or acrylate. Examples of useful R' groups are as described above.

Subscript y is an integer from 3 to 30, preferably from 3 to 10. Subscript y'is an integer from 1 to 500, preferably from 1 to 200.

Component (iii) may be added in amounts from 0 to 45,000 parts by weight per 100 parts by weight of component (i), preferably 0 to 1000 parts by weight on the same basis, more preferably 100 to 1000 parts by weight on the same basis. Component (iii) may be a single species or a mixture of different species. It may also comprise materials described solely by formula (V) or formula (VI) or mixtures thereof. Component (iii) is commercially available or may be made by methods known in the art.

It is preferred that if component (i) is a reaction product and it does not contain any silicon-bonded hydrogen bonds then at least one R' of either component (ii) or (iii) is hydrogen so Si-H containing branched polymers are formed.

Although specific functional groups are described above, generally the only limitation on the functional group is the ability of the particular functional group to withstand the desired equilibration conditions employed. Those knowledgeable in the art can select the appropriate combination of functionality, catalyst and conditions to ensure reaction.

The catalyst used in the present method can be any of a wide variety of acidic catalysts known in the art to be useful for the ring opening polymerization of cyclosiloxanes. Examples of some appropriate types of catalysts for Si-H functional equilibrations include sulfuric acid, trifluoromethanesulfonic acid, acidic phosphazenes, acid clays and acidic ion exchange resins. Preferred catalyst include triflic acid and acid ion exchange resins.

The amount of catalyst, excluding any inert supporting material, that is useful ranges from about 10 parts per million (ppm) to 2 parts by weight based on total weight percent solids (all non-solvent ingredients) in the composition. While polymerization can be achieved by using more or less than these amounts of an acid catalyst, this is not practical, as in the former case excessive amounts of acid would be required for neutralization of the catalyst at the end of the reaction, while in the latter case the use of only trace amounts of catalyst could hinder its effectiveness in the initial reaction.

The catalyst may be a single species or a mixture of different species. Component (ii) is commercially available or may be made by methods known in the art.

Except for the presence of the organohydrogensilicon compounds used as component (i) or used to make the reaction product of component (i) in the method of preparing branched polymers according to this invention, the method employed herein is generally known in the art. U.S. Pat. No. 2,868,766, U.S. Pat. No. 2,994,684, and U.S. Pat. No. 3,002,951 each of which is hereby incorporated by reference, relate to methods of making various types of polymers by polymerizing and copolymerizing cyclic type siloxane species at elevated temperatures, in the presence of a catalyst, for a time sufficient to obtain the desired state of polymerization.

Thus, for example, polymerization of components (i), (ii), and optionally (iii) can be carried out at a temperature ranging from 30 to 250° C for a time ranging from 5 minutes to three days. Generally, polymerization can be accelerated by increasing the reaction temperature.

While it is preferred to carry out the reaction in the absence of a solvent, the reaction can be conducted in the presence of solvents such as acetonitrile, dimethylformamide, decahydronaphthalene, toluene, p-chloro-toluene, o-dichloro-benzene, tetrahydrofuran, xylene, dimethyl sulfoxide, or dibutyl ether, if desired.

Any of the essential and optional components used in carrying out the polymerization reaction can be combined in stoichiometric quantities necessary to achieve the desired distribution of repeating units in the polymer chain of the polymer composition.

The Si-H containing branched polymers made by the present method may be used as is or they may be further reacted. An optional step (2) of the present method is to hydrosilylate the Si-H containing branched polymers produced by step (1) to form branched polymers. This step (2) comprises mixing in the presence of a platinum group metal-containing catalyst, the polymers from step (1) with (iv) at least one material having at least one aliphatic unsaturation.

Component (iv) comprises at least one material having at least one aliphatic unsaturation. The materials of Component (iv) can be linear, branched, resinous or cyclic and can be monomers or polymers (including copolymers, terpolymers etc.) provided there is at least one aliphatic unsaturation. Materials containing aliphatic unsaturation which are useful in the present invention have alkenyl (also described as olefinic) unsaturation or alkynyl (also described as acetylenic) unsaturation. These materials are well-known in the art of hydrosilylation and are disclosed in such patents as U.S. Pat. No. 3,159,662 (Ashby), U.S. Pat. No. 3,220,972 (Lamoreaux)), and U.S. Pat. No. 3,410,886 (Joy), which disclosures of said materials are incorporated herein by reference. In instances where these unsaturated materials contain elements other than carbon and hydrogen, it is preferred that these elements be oxygen, nitrogen, silicon, a halogen, or a combination thereof.

The aliphatically unsaturated material of component (iv) can contain one or more carbon-carbon multiple bonds. Representative examples of the aliphatically unsaturated hydrocarbons which can be employed include mono-olefins, for example, ethene (ethylene), propene, and 1-pentene, diolefins, for example, divinylbenzene, butadiene, 1,5-hexadiene and 1-buten-3-yne, cycloolefins, for example, cyclohexene and cycloheptene, and monoalkynes, for example, acetylene, propyne and 1-hexyne.

Oxygen-containing aliphatically unsaturated c materials can also be used for component (iv), especially where the unsaturation is ethylenic, such as vinylcyclohexyl epoxide, allyl glycidyl ether, methylvinyl ether, divinylether, phenylvinyl ether, monoallyl ether of ethylene glycol, allyl aldehyde, methylvinyl ketone, phenylvinyl ketone, acrylic acid, methacrylic acid, methyl acrylate, allyl acrylate, methyl methacrylate, allyl methacrylate, vinylacetic acid, vinyl acetate, and linolenic acid.

Heterocyclic compounds containing aliphatic unsaturation in the ring, such as dihydrofuran, and dihydropyran, are also suitable as component (iv).

Halogenated derivatives of the previously mentioned aliphatically unsaturated materials can be employed as component (iv), including acyl chlorides as well as materials containing a halogen substituent on a carbon atom other than a carbonyl carbon atom. Such halogen-containing materials include, for example, vinyl chloride, and the vinylchlorophenyl esters.

Unsaturated materials containing nitrogen substituents such as acrylonitrile, N-vinylpyrrolidone, alkyl cyanide, nitroethylene, etc., are also useful.

Other materials useful as component (iv) in the practice of the present method include polymers (including copolymers, terpolymers etc.) of the various materials described above provided there is at least one aliphatic unsaturation. Examples include polymers derived from olefinic monomers having 2 to 20 carbon atoms and dienes having 4 to 20 carbon atoms; polymers of monoolefin, isomonoolefin and vinyl aromatic monomers, such as monoolefins having 2 to 20 carbon groups, isomonoolefins having 4 to 20 carbon groups, and vinyl aromatic monomers including styrene, para-alkylstyrene, para-methylstyrene. The materials can also be poly(dienes) and derivatives. Most polymers derived from dienes usually contain unsaturated ethylenic units on backbone or side-chains. Representative examples include polybutadiene, polyisoprene, polybutenylene, poly(alkyl-butenylene) where alkyl includes alkyl groups having 1 to 20 carbon atoms, poly(phenyl-butenylene), polypentenylene, natural rubber (a form of polyisoprene); and butyl rubber (copolymer of isobutylene and isoprene). The polymers can also contain oxyhydrocarbon repeating units such as poly(alkyleneglycol) polymers end-capped with allyloxy or vinyoxy groups. Common examples are polymers and copolymers of ethylene glycol and/or propylene glycol.

The materials of component (iv) can also be a halogenated olefin polymer having aliphatic unsaturation. Representative examples of a halogenated olefin polymer having aliphatic unsaturation include polymers resulting from the bromination of a copolymer of isomonoolefin with para-methylstyrene to introduce benzylic halogen (as described in U.S. Pat. No. 5,162,445), halogenated polybutadienes, halogenated polyisobutylene, poly(2-chloro-1,3-butadiene), polychloroprene (85% trans), poly(1-chloro-1-butenylene) (Neoprene™), and chlorosulfonated polyethylene.

The materials of component (iv) having aliphatic unsaturation can also include polymers containing other compounds described above such as vinyl ether groups, acrylate groups, methyacrylate groups, and epoxy-functional groups.

A particularly useful type of material which can be employed as component (iv) in the present method is that containing silicon, such as those compounds commonly referred to as organosilicon compounds and silicon modified organic compounds. The useful organosilicon materials have at least one aliphatically unsaturated group attached to silicon per molecule. The aliphatically unsaturated organosilicon materials include silanes, polysilanes, siloxanes, silazanes, as well as monomeric or polymeric materials containing silicon atoms joined together by hydrocarbyl groups such as alkylene or polyalkylene groups or arylene groups. The silicon-modified organic materials useful in the present invention include organic monomers or polymers such as described above having at least one silicon atom attached as a silane or a siloxane segment. The silicon-containing units can contain aliphatic unsaturation and can be attached at the terminal and/or pendant positions on the organic polymer chain or as a copolymer.

Silanes useful in the present invention can be described by formula (VII)

$$Q_{4-w}R^1_wSi,$$

where each $R^1$ is an independently selected monovalent hydrocarbon radical comprising 1 to 20 carbon atoms free from aliphatic unsaturation, each Q is independently selected from a monovalent hydrocarbon group comprising 2 to 20 carbon atoms having at least one aliphatic unsaturation, a monovalent oxyhydrocarbon group comprising 2 to 20 carbon atoms having at least one aliphatic unsaturation, a halogen atom, an alkoxy group, or an acyl group, provided at least one Q group has at least one aliphatic unsaturation, and w is an integer from 0 to 3.

Examples of silanes include vinyltrimethoxysilane, vinyltriethoxysilane, vinyltrimethylsilane, vinyldimethylchlorosilane, vinylmethyldichlorosilane, divinyldimethylsilane, diallyldimethylsilane, hexenyldimethylchlorosilane, and hexenylmethyldichlorosilane, and vinyltriacetoxysilane.

Examples of silane-modified organic polymers are silylated polymers derived from olefins, isomonoolefin, dienes, ethylene or propylene oxides, and vinyl aromatic monomers having 2 to 20 carbon atoms such as the silane-grafted copolymers of isomonoolefin and vinyl aromatic monomer as discussed in U.S. Pat. Nos. 6,177,519 and 5,426,167. Other representative silicon-modified organic polymers are illustrated by, but not limited to alkenylsiloxy-functional polymers such as vinylsiloxy-, allylsiloxy-, and hexenylsiloxy-organic polymers and siloxane-organic block copolymers.

Preferred organosilicon polymers and silicon-modified organic polymers can be described by formula (VIII):

$$(Q_{3-n}'R^1_n'SiO_{1/2})_{c'}(Q_{2-o}'R^1_o'SiO_{2/2})_{d'}(Q_{1-p}'R^1_p'SiO_{3/2})_{e'}(SiO_{4/2})_{f'}(CR^2_qQ_{1-q'})_{g'}(CR^2_{r'}Q_{2-r'})_{h'}(O(CR^2_sQ_{2-s'}))_{i'}(CR^2_tQ_{3-t'})_{j'}$$

where each $R^1$ and Q group is as described above, each $R^2$ is an independently selected hydrogen atom or monovalent hydrocarbon group comprising 1 to 20 carbon atoms which are free from aliphatic unsaturation, the sum of c'+d'+e'+f'+g'+h'+i'+j' is at least 2, n' is an integer from 0 to 3, o' is an integer from 0 to 2, p' is an integer from 0 to 1, q' is an integer from 0 to 1, r' is an integer from 0 to 2, s' is an integer from 0 to 2, t' is an integer from 0 to 3, provided if g'+h'+i'+j'>0 then c'+d'+e'+f>0.

In formulas (VII) and (VIII), each $R^1$ group is an independently selected monovalent hydrocarbon group comprising 1 to 20 carbon atoms which are free from aliphatic unsaturation. Each $R^1$ group can be linear, branched or cyclic. $R^1$ can be unsubstituted or substituted with halogen atoms. The monovalent hydrocarbon group of $R^1$ can be exemplified by alkyl groups such as methyl, ethyl, propyl, butyl, hexyl, octyl, 3,3,3-trifluoropropyl, chloromethyl, and decyl, cycloaliphatic groups such as cyclohexyl, aryl groups such as phenyl, tolyl, and xylyl, chorophenyl, and aralkyl groups such as benzyl, styryl and alpha-methylstyryl. It is preferred that each $R^1$ group is an independently selected alkyl group comprising 1 to 8 carbon atoms or aryl group comprising 6 to 9 carbon atoms. It is most preferred that each $R^1$ group is independently selected from methyl, alpha-methylstyryl, 3,3,3-trifluoropropyl and nonafluorobutylethyl. Each $R^1$ can be identical or different, as desired.

In formula (VIII), each $R^2$ group is an independently selected hydrogen atom or monovalent hydrocarbon group comprising 1 to 20 carbon atoms free from aliphatic unsaturation. Each monovalent hydrocarbon groups of $R^2$ can be linear, branched or cyclic. Each monovalent hydrocarbon group of $R^2$ can be unsubstituted or substituted with halogen atoms. The monovalent hydrocarbon groups of $R^2$ are exemplified as described above for the monovalent hydrocarbon groups of $R^1$. It is preferred that each $R^2$ group is an independently selected hydrogen atom, alkyl group comprising 1 to 8 carbon atoms, or aryl group comprising 6 to 9 carbon atoms. It is most preferred that each $R^2$ is hydrogen. Each $R^2$ can be identical or different, as desired.

In formulas (VII) and (VIII), each Q is independently selected from a monovalent hydrocarbon group comprising 2 to 20 carbon atoms having at least one aliphatic unsaturation, a monovalent oxyhydrocarbon group comprising 2 to 20 carbon atoms having at least one aliphatic unsaturation, a halogen atom, an alkoxy group, or an acyl group, provided at least one Q group has at least one aliphatic unsaturation.

The aliphatic unsaturations of Q can be found in a pendant position to the hydrocarbon chain, at the end of the hydrocarbon chain, or both, with the terminal position being preferred. Each monovalent hydrocarbon and oxyhydrocarbon group can be linear, branched, or cyclic.

Examples of monovalent hydrocarbon groups comprising 2 to 20 carbon atoms having at least one aliphatic unsaturation of Q include alkenyl groups such as vinyl, allyl, 3-butenyl, 4-pentenyl, 5-hexenyl, cyclohexenyl, 6-heptenyl, 7-octenyl, 8-nonenyl, 9-decenyl, 10-undecenyl, and diene groups comprising 4 to 20 carbon atoms such as 4,7-octadienyl, 5,8-nonadienyl, 5,9-decadienyl, 6,11-dodecadienyl, 4,8-nonadienyl, and 7,13-tetradecadienyl.

Examples of monovalent oxyhydrocarbon groups comprising 2 to 20 carbon atoms having at least one aliphatic unsaturation of Q include alkenyloxy groups such as oxybutylvinylether and alkynyloxy groups such as propargyloxy or hexynyloxy.

Examples of halogen atoms of Q include chloro, fluoro, and bromo atoms. Examples of alkoxy groups of Q include methoxy, ethoxy, and isopropoxy. An example of an acyl group of Q is acetoxy.

Preferably, each Q is an independently selected monovalent hydrocarbon group comprising 2 to 20 carbon atoms having at least one aliphatic unsaturation. More preferably, each Q is an independently selected alkenyl group comprising 2 to 20 carbon atoms, with an alkenyl group comprising 2 to 8 carbon atoms being most preferred for Q.

In formula (VIII), the sum of c'+d'+e'+f'+g'+h'+i'+j' is at least 2, preferably from 2 to 5300, more preferably from 2 to 1000. Preferably, subscript c' is an integer from 0 to 50, with 2 to 20 being more preferred, and 2 to 10 being most preferred. Preferably, subscript d' is an integer from 0 to 5000, with 0 to 500 being more preferred, and 1 to 300 being most preferred. Preferably, subscript e' is an integer from 0 to 48, with 0 to 30 being more preferred, and 0 to 15 being most preferred. Preferably, subscript f' is an integer from 0 to 24, with 0 to 10 being more preferred, and 0 to 6 being most preferred. Preferably, subscript g' is an integer from 0 to 50, with 0 to 20 being more preferred, and 0 to 10 being most preferred. Preferably, subscript h' is an integer from 0 to 150, with 0 to 80 being more preferred, and 0 to 60 being most preferred. Preferably, subscript i' is an integer from 0 to 50, with 0 to 20 being more preferred, and 0 to 10 being most preferred. Preferably, subscript j' is an integer from 0 to 50, with 0 to 15 being more preferred, and 0 to 10 being most preferred.

In formula (VIII), n' is an integer from 0 to 3, preferably from 2 to 3; o' is an integer from 0 to 2, preferably from 1 to 2; p' is an integer from 0 to 1, preferably 1; q' is an integer from 0 to 1, preferably 1; r' is an integer from 0 to 2, preferably from 1 to 2; s' is an integer from 0 to 2, preferably from 1 to 2; and t' is an integer from 0 to 3, preferably from 2 to 3.

Examples of organosilicon polymers and silicon-modified organic polymers described by formula (VIII) include trimethylsiloxy-terminated polydimethylsiloxane-polymethylvinylsiloxane copolymers, vinyldimethylsiloxy-terminated polydimethylsiloxane-polymethylvinylsiloxane copolymers, trimethylsiloxy-terminated polydimethylsiloxane-polymethylhexenylsiloxane copolymers, hexenyldimethylsiloxy-terminated polydimethylsiloxane-polymethylhexenylsiloxane copolymers, vinyldimethylsiloxy-terminated polydimethylsiloxane-polymethyhexenylsiloxane copolymers, trimethylsiloxy-terminated polymethylvinylsiloxane polymers, trimethylsiloxy-terminated polymethylhexenylsiloxane polymers, vinyldimethylsiloxy-terminated polydimethylsiloxane polymers, and hexenyldimethylsiloxy-terminated polydimethylsiloxane polymers, vinyldimethylsiloxy terminated poly(dimethylsiloxane-monomethylsilsesquioxane) polymers, vinyldimethylsiloxy terminated poly(dimethylsiloxane-vinylmethylsiloxane-methylsilsesquioxane) copolymers; trimethylsiloxy terminated poly(dimethylsiloxane-vinylmethylsiloxane-methylsilsesquioxane) polymers, hexenyldimethylsiloxy terminated poly(dimethylsiloxane-monomethylsilsesquioxane) polymers, hexenyldimethylsiloxy terminated poly(dimethylsiloxane-hexenylmethylsiloxane-methylsilsesquioxane) copolymers; trimethylsiloxy terminated poly(dimethylsiloxane-hexenylmethylsiloxane-methylsilsesquioxane) polymers, vinyldimethylsiloxy terminated poly(dimethylsiloxane-silicate) copolymers, hexenyldimethylsiloxy-terminated poly(dimethylsiloxane-silicate) copolymers, trimethylsiloxy terminated poly (dimethylsiloxane-vinylmethylsiloxane-silicate) copolymers and trimethylsiloxy terminated poly(dimethylsiloxane-hexenylmethylsiloxane-silicate) copolymers, vinylsiloxy or hexenylsiloxy terminated poly(dimethylsiloxane-hydrocarbyl copolymers), vinylsiloxy terminated or hexenylsiloxy terminated poly(dimethylsiloxane—polyoxyalkylene) block copolymers, alkenyloxydimethylsiloxy terminated polyisobutylene and alkenyloxydimethylsiloxy terminated polydimethylsiloxane-polyisobutylene block copolymers.

Examples of preferred Component (iv) materials include hexenyldimethylsiloxy-terminated polydimethylsiloxane-polymethylhexenylsiloxane copolymers, hexenyldimethylsiloxy-terminated polydimethylsiloxane polymers, vinyldimethylsiloxy-terminated polydimethylsiloxane polymers, vinyl or hexenyldimethylsiloxy-terminated poly(dimethylsiloxane-silicate) copolymers and vinyl or hexenyldimethylsiloxy terminated poly(dimethylsiloxane-hydrocarbyl) copolymers, having a degree of polymerization (Dp) of from 25 to 500 and a viscosity at 25° C. of from 50 to 3,000 millipascal-seconds (mPa.s).

It is more preferred that Component (iv) is a material selected from hexenyldimethylsiloxy-terminated polydimethylsiloxane-polymethylhexenylsiloxane copolymers, vinyldimethylsiloxy-terminated polydimethylsiloxane polymers, vinyldimethylsiloxy-terminated poly(dimethylsiloxane-silicate) copolymers each having a Dp of from 50 to 300 and a viscosity at 25° C. of from 80 to 1,000 mPa.s.

Component (iv) comprises at least one material having at least one aliphatic unsaturation. This means Component (iv) may be one compound having at least one aliphatic saturation or a mixture of different compounds. Component (iv) can also have one or more aliphatic unsaturations. In preferred embodiments, component (A) comprises at least one compound having at least two aliphatic unsaturations. Most preferred is when component (iv) comprises one compound having at least two aliphatic unsaturations The platinum group metal-containing catalyst useful in optional step (2) of the present method has been described above with respect to the preparation of the reaction product of component (i).

Another embodiment of the present invention comprises the Si-H containing branched polymers and the branched polymers prepared by the method claimed herein. Another embodiment includes compositions comprising the Si-H containing branched polymers and/or the branched polymers prepared by the method claimed herein. A specific preferred composition comprises Si-H containing branched polymers made by the present method, Si-alkenyl crosslinker, platinum-group containing catalyst, inhibitor and optionally release modifier and additives for e.g. anchorage. These ingredients, other than the Si-H containing branched polymers made by the present method, are all well known in the art The Si-H containing branched polymers and the branched polymers prepared by the present method are particularly useful because they enable the production of low viscosity, high Dp, branched polymers. In addition, due to the use of a cyclic branched intermediate without end-groups, it is possible to independently control the properties of branching, end-group level, end-group identity, and Dp. Among other uses, these polymers can be used as fluids, crosslinkers, release polymers, anchorage additives, refractive index modifiers, etc.

The following examples are disclosed to further teach, but not limit, the invention, which is properly delineated by the appended claims.

EXAMPLES

Silicon 29 Nuclear Magnetic Spectroscopy ($^{29}$Si NMR) $^{29}$Si NMR data was collected on a Varian Mercury 300 using chloroform D solvent. The experiment was conducted with a relaxation delay of 60 sec with a gated decoupled pulse sequence using a 5 mm switchable PFG probe was used. Alternatively, the sample was run on a Mercury 400 using a Nalorac 16 mm silicon free Pulsetune® probe with 0.03 M Cr(acac)$_3$ as a relaxation reagent and gated decoupling to ensure quantitative conditions. Both used 90 degree pulsewidth and the 400 used a 12 sec relaxation delay.

Si-H Measurement—The material was measured out (according to estimated Si-H content) in 125 mL Erlenmeyer flask to nearest 0.01 grams and sample weight recorded. To this was added 20 mL of prepared mercuric acetate solution (4% mercury acetate powder, 96% (1:1 mixture) methanol/chloroform), the flask was then covered and swirled to mix. A blank sample (no Si-H containing material added) was also prepared for comparison. After samples stood for 30 minutes, they were quenched with 20 mL of prepared calcium chloride solution (25% calcium chloride, 75% methanol). Then 10 drops of prepared phenolphthalein solution (1% phenolphthalein in ethanol) from small pipet was added. The samples were then titrated with 0.1N methanolic potassium hydroxide and measurements taken.

Vinyl Titration: A sample was weighed to the nearest 0.01 g into a 250 mL iodine flask. Methylene chloride (50.00 mL) was added to dissolve the sample, followed by iodine monochloride (20.00 mL). The sample is placed in the dark for 2 hours. After this period, KI solution (10% KI in DI water; 15.0 mL) is added followed by DI water (50.0 mL). The contents of the flask are swirled to mix well, then the liberated iodine titrated with sodium thiosulfate solution (0.1N in DI water).

Gel Permeation Chromatography (GPC)—GPC data was collected using a Waters 515 pump, a Water 717 autosampler and a Waters 2410 differential refractometer. The separation was made with two (300 mm×7.5 mm) Polymer Laboratories Plgel 5 um Mixed-C columns, preceded by a Plgel 5 um guard column. HPLC grade toluene eluent was used at 1.0 mL/min flowrate and columns and detector were heated to 45° C. An injection volume of 50 uL was used and the sample prefiltered through a 0.45 um PTFE syringe filter. Molecular weight averages were determined relative to a calibration curve ($4^{th}$ order) created using polydimethylsiloxane (PDMS) standards covering the molecular weight range of 1300-850,000.

Measurement of Cure—To measure cure based on percent extractable silicone, a sample of silicone-coated substrate was taken in the form of a circular disk. After obtaining an initial coat weight measurement on the sample by X-ray fluorescence (XRF) on an Oxford Lab-X3000 Benchtop XRF Analyzer, it was submerged in methylisobutyl ketone (MIBK), with agitation, for 30 minutes. After MIBK extraction, the sample was removed from the MIBK solvent, allowed to air dry and a second coat weight measurement acquired. The percent extractable silicone is defined as the percent loss in silicone coat weight.

Preparation of Organohydrogensilicon Compound

To a reaction vessel was added 2947 g of a poly(methylhydrogen) cyclic siloxane (MeH cyclics) having an average Dp of about 4.4 (49.1 moles Si-H) and 5053 g of a dimethylvinylsiloxy end-blocked polydimethylsiloxane polymer having an average Dp of about 8 (14.4 moles vinyl) to give an Si-H/SiVi ratio of 3.4:1. The polymers were well mixed and a vinylsiloxane diluted platinum (Pt) catalyst added to give a Pt content of about 12 ppm. An exothermic reaction was initiated and over a period of 10 minutes the temperature of the vessel contents rose from 25° C. to 137° C. After cooling for 2 hours, bis(2-methoxy-1-methylethyl)maleate (80 g, 1 wt %) was added to stabilize the Pt from further activity. The resulting polymer was not stripped and was shown by GC to have a remaining unreacted MeH cyclics content of about 4%. The isolated product had a viscosity of 78 mPa.s, a Si-H level of 0.42 wt % (Si-H as H) as determined by titration and a GPC Mn=2810 and Mw=8115 vs polydimethylsiloxane (PDMS) standards. $^{29}$Si NMR analysis of the product demonstrated that all vinyl functionality has been consumed yielding silethylene bridges, no ring opening has occurred and that the resulting molecular structure is consistent with a methylhydrogen cyclic siloxane capped linear siloxane polymer as described below, where Me is methyl, x is an average of 6.5 for Mw and an average of 1.5 for Mn and d is an average of about 8.

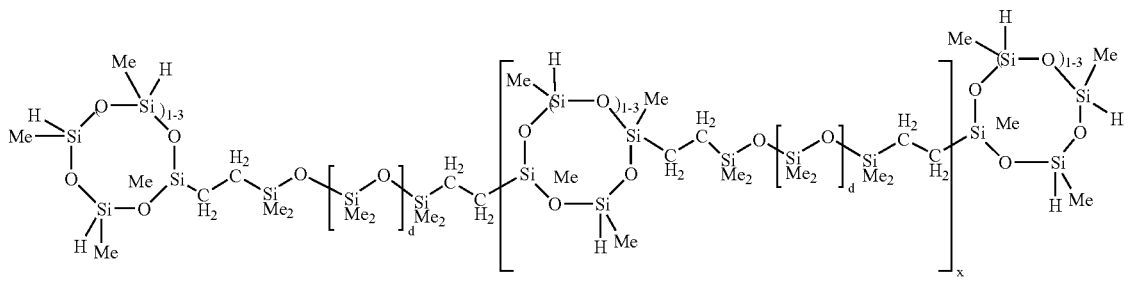

Preparation of Branched Intermediate A

A 2 L 3 neck flask was equipped with a condenser, stirrer, thermometer, nitrogen purge and addition funnel. Methyl hydrogen cyclics of avg. Dp=4.4 (319.2 g, 5.3 mol Si-H) along with vinyl terminated polydimethylsiloxane of avg. Dp=8 (547.3 g, 1.74 mol Vi) were added to the flask and well mixed. A siloxane complexed Pt catalyst was added to provide a Pt level of 12 ppm. An exothermic reaction was initiated and the temperature of the reactants quickly rose to 132° C. over about 10 minutes. After the exotherm had subsided, the mixture was cooled to 45° C. and 1-hexene (331.4 g, 3.9 mol Vi) was added dropwise to keep the exotherm controlled between 35-50° C. After addition was complete, the reaction mixture was cooled to 25° C. and stripped at 150° C./1 mm Hg to remove volatile material. The reaction product (Intermediate A) was clear, slightly viscous and had an amber tint. Analysis of the branched polymer produced with this intermediate confirms that synthesis of the desired hexyl capped intermediate was achieved.

Preparation of Branched Intermediate B

A 3 neck flask equipped with stirrer, nitrogen purge and thermometer was charged with methylhydrogencyclosiloxanes (Avg Dp=4.4; 62.2 g, 1.04 mol SiH) and vinyl terminated polydimethylsiloxane (Dp=7, 106.8 g, 0.31 mol Vi). The mixture was stirred well and then catalyzed with 0.2 g of a 1% w/w Pt/C catalyst. The mixture was heated to 60°C. to initiate an exothermic reaction. The heat source was removed; the temperature rose to 140° C. before slowly cooling to room temperature. The product was pressure filtered through filter aid on a 0.45 nylon filter to yield a clear, water white fluid of 77 cP. The % SiH(as H) was measured to be 0.36% by weight. Pt analysis by digestion/ICP showed a non-detectable level of Pt with a detection limit of 1 ppm.

Example 1

Synthesis of SiH Containing Branched Polymer

A 2 L 3 neck flask was equipped with a condenser, stirrer, nitrogen purge and thermometer. To the flask was added Branched Intermediate A, the desired end-blocker and dimethyl cyclic siloxanes (mixture of $D_4$ and $D_5$) and the triflic acid catalyst. The equilibration reaction was conducted at 80° C. for 5 hours, then cooled to room temperature before addition of calcium carbonate. The polymers were stripped at 130° C./1 mm Hg using a wiped film evaporater. The stripped polymer was filtered through a pressure filter containing a glass fiber filter and optionally filter aid or calcium carbonate. GPC, $^{29}$Si NMR and $^{13}$C NMR data on the SiH containing branched polymer supports the polymer structures indicated in Table 1.

Examples 2 and 3

Synthesis of SiH Containing Branched Polymer

A 3 neck flask was equipped with a condenser, stirrer, nitrogen purge and thermometer. To the flask was added the desired branched intermediate, the desired end-blocker and dimethyl cyclic siloxanes (mixture of $D_4$ and $D_5$) and the catalyst. The equilibration reaction was conducted at 80° C. for 5 hours, then cooled to room temperature before addition of calcium carbonate or decantation from the ion exchange resin. The polymers were stripped at 130° C./1 mm Hg using a wiped film evaporater. The stripped polymer was filtered through a pressure filter containing a glass fiber filter and optionally filter aid or calcium carbonate. GPC, $^{29}$Si NMR and $^{13}$C NMR data on the SiH containing branched polymer supports the polymer structures indicated in Table 2.

TABLE 1

| | Branched Intermediate (g) | Endblocker (g) | Dimethyl Cyclics (g) | Acid catalyst (g) | Base Neutralization | Dp | Branch units | Endblock Group | % Vinyl | Viscosity (cP) |
| --- | --- | --- | --- | --- | --- | --- | --- | --- | --- | --- |
| Ex 1 | (A), 52.8 | Tetramethyl-disiloxane, 6.2 | 244.1 | 0.43 triflic acid | Calcium carbonate | 300 | 6 | SiMe$_2$H | | 152 |

TABLE 2

| | Branched Intermediate | Endblocker | Dimethyl Cyclics (g) | Acid catalyst (g) | Base Neutralization | Dp | Branch units | Endblock Group | Viscosity (cP) | % SiH |
| --- | --- | --- | --- | --- | --- | --- | --- | --- | --- | --- |
| Ex 2 | (A) 53.0 g | Tetramethyl-disiloxane, 6.2 (g) | 241.0 | Dowex ® 2040 Ion Exchange Resin, 2.4 g | Decantation | 200 | 4 | SiMe2H | 110 | 0.03 |

TABLE 2-continued

| | Branched Intermediate | Endblocker | Dimethyl Cyclics (g) | Acid catalyst (g) | Base Neutralization | Dp | Branch units | Endblock Group | Viscosity (cP) | % SiH |
|---|---|---|---|---|---|---|---|---|---|---|
| Ex 3 | (B) 47.6 g | Tetramethyldisiloxane, 8.2 g | 318.0 | Dowex ® 2040 Ion Exchange Resin, 2.4 g | Decantation | 300 | 7 | SiMe2H | 110 | 0.07 on polymer, 0.11% including residual cyclics |

Polymer Coating and Curing

The Si-H containing branched polymer made in Examples 3 was mixed with vinyl polymer, catalyst, and inhibitor in the amounts described below. The coating composition was applied to the specified substrate in sheet form using a pressure blade coater and cured immediately in an oven equipped with a moving web. The cure/release data is summarized in Table 3.

| | |
|---|---|
| Polymer(dimethylvinylsiloxy endblocked polydimethylsiloxane silicate copolymer of 160 Dp) | 10.0 g |
| Crosslinker - Example 3 (Si—H containing branched polymer) | 4.3 g |
| Inhibitor - Ethynylcyclohexanol | 0.06 g |
| Catalyst - Pt in siloxane | 0.28 g |
| Cure temp./time | 149° C. (300° F.)/6 sec |
| SiH/SiVi ratio | 1.6 |
| Substrate | SCK paper |

TABLE 3

| Example | Structure Dp/branches/endgroup | Extractable silicone(%) | Release Force(g/in) @ 12 in/min; TESA® 7475 adhesive* | Release Force (g/in) @ 4000 in/min, TESA® 7475 adhesive |
|---|---|---|---|---|
| Example 3 | 300/7/Me2SiH | 3.7 | 27 | 87 |

TESA® 7475 Adhesive is a solvent acrylic adhesive available in a tape format.

The invention claimed is:

1. A method comprising (1) heating in the presence of an acidic cyclosiloxane ring opening polymerization catalyst, a mixture comprising
   (i) at least one organohydrogensilicon compound containing at least one silicon-bonded hydrogen atom per molecule or a reaction product obtained by mixing in the presence of a platinum group metal-containing catalyst at least one organohydrogensilicon compound containing at least one silicon-bonded hydrogen atom per molecule and at least one compound having at least one aliphatic unsaturation where in each case the organohydrogensilicon compound is described by formula (I)

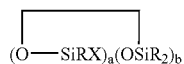

where each R is independently selected from a hydrogen atom and a monovalent hydrocarbon group comprising 1 to 20 carbon atoms which is free from aliphatic unsaturation, a is an integer from 1 to 18, b is an integer from 1 to 19, a+b is an integer from 3 to 20, each X is an independently selected functional group selected from a halogen atom, an ether group, an alkoxy group, an alkoxyether group, an acyl group, a silyl group, or a —Z—R$^4$ group, where each Z is independently selected from an oxygen and a divalent hydrocarbon group comprising 2 to 20 carbon atoms, each R$^4$ group is independently selected from —BR$_u$Y$_{2-u}$, —SiR$_v$Y$_{3-v}$, or a group described by formula (II):

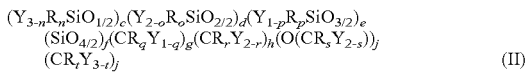

where B refers to boron, each R is as described above, the sum of c+d+e+f+g+h+i+j is at least 2, n is an integer from 0 to 3, o is an integer from 0 to 2, p is an integer from 0 to 1, q is an integer from 0 to 1, r is an integer from 0 to 2, s is an integer from 0 to 2, t is an integer from 0 to 3, u is an integer from 0 to 2, v is an integer from 0 to 3, each Y is an independently selected functional group selected from a halogen atom, an ether group, an alkoxy group, an alkoxyether group, an acyl group, a silyl group, or a Z-G group, where Z is as described above, each G is a cyclosiloxane described by formula (III):

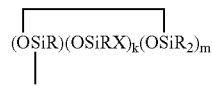

where R and X are as described above, k is an integer from 0 to 18, m is an integer from 0 to 18, k+m is an integer from 2 to 20, provided in formula (II) that one of the Y groups is replaced by the Z group bonding the R$^4$ group to the cyclosiloxane of formula (I), and provided further at least one X group of Formula (I) is a —Z—R$^4$ group;
   (ii) at least one endblocker described by formula (IV) R'$_3$SiO(MeR'SiO)$_z$SiR'$_3$, where z ranges from 0 to 150 and each R' is independently chosen from hydrogen, alkyl, aryl, alkenyl, dienyl or functional alkyls where the functionality may be fluoro, fluoroether, polyether, ether, aryl, silyl, siloxy, carboxy, glycosidyl or acrylate, and optionally
   (iii) at least one organosiloxane chosen from a hydrolyzate described by formula (V) HO(MeR'SiO)$_y$'H and a cyclosiloxane described by formula (VI) (MeR'SiO)$_{y'}$, where y is an integer from 3 to 30, y' is an integer from 1 to 500, and each R' is as described above;
   provided if component (i) is a reaction product and it does not contain any silicon-bonded hydrogen bonds then at least one R' of either component (ii) or (iii) is hydrogen,
   so to cause polymerization of components (i), (ii), and optionally (iii) to form silicon-bonded hydrogen containing branched polymers.

2. The method of claim 1 where subscript b is an integer from 2 to 19, subscript c is an integer from 0 to 50, subscript d is an integer from 0 to 5000, subscript e is an integer from 0 to 48, subscript f is an integer from 0 to 24, subscript g is an integer from 0 to 50, subscript h is an integer from 0 to 50, subscript i is an integer from 0 to 50, and subscript j is an integer from 0 to 50.

3. The method of claim 1 where each R group is independently selected from hydrogen atoms, alkyl groups comprising 1 to 8 carbon atoms, or aryl groups comprising 6 to 9 carbon atoms, each X is a Z-$R^4$ group or is independently selected from chloro, methoxy, isopropoxy, where Z is a divalent hydrocarbon group, and $R^4$ is selected from —$CH_2CH_2$—, —$CH_2CH_2CH_2CH_2$—, —$O(CH_2CH_2O)_{z'}$—, where $z'$=1-100, $O(CH_2CH_2CH_2O)_{z''}$—, where $z''$=1-100 and siloxane groups described by —$R_2SiO(R_2SiO)_dSiR_2$—Z-G, —$R_2SiOSiR_3$, —$R_2SiOSiR_2$-Y, and —$RSi(OSiR_3)_2$, where d is an integer from 1 to 50 and Z, G, and R are as described above.

4. The method of claim 1 where the organohydrogensilicon compound is selected from the structures below where Me is methyl, $d_1+d_2=d$, and x is an integer from 1 to 100:

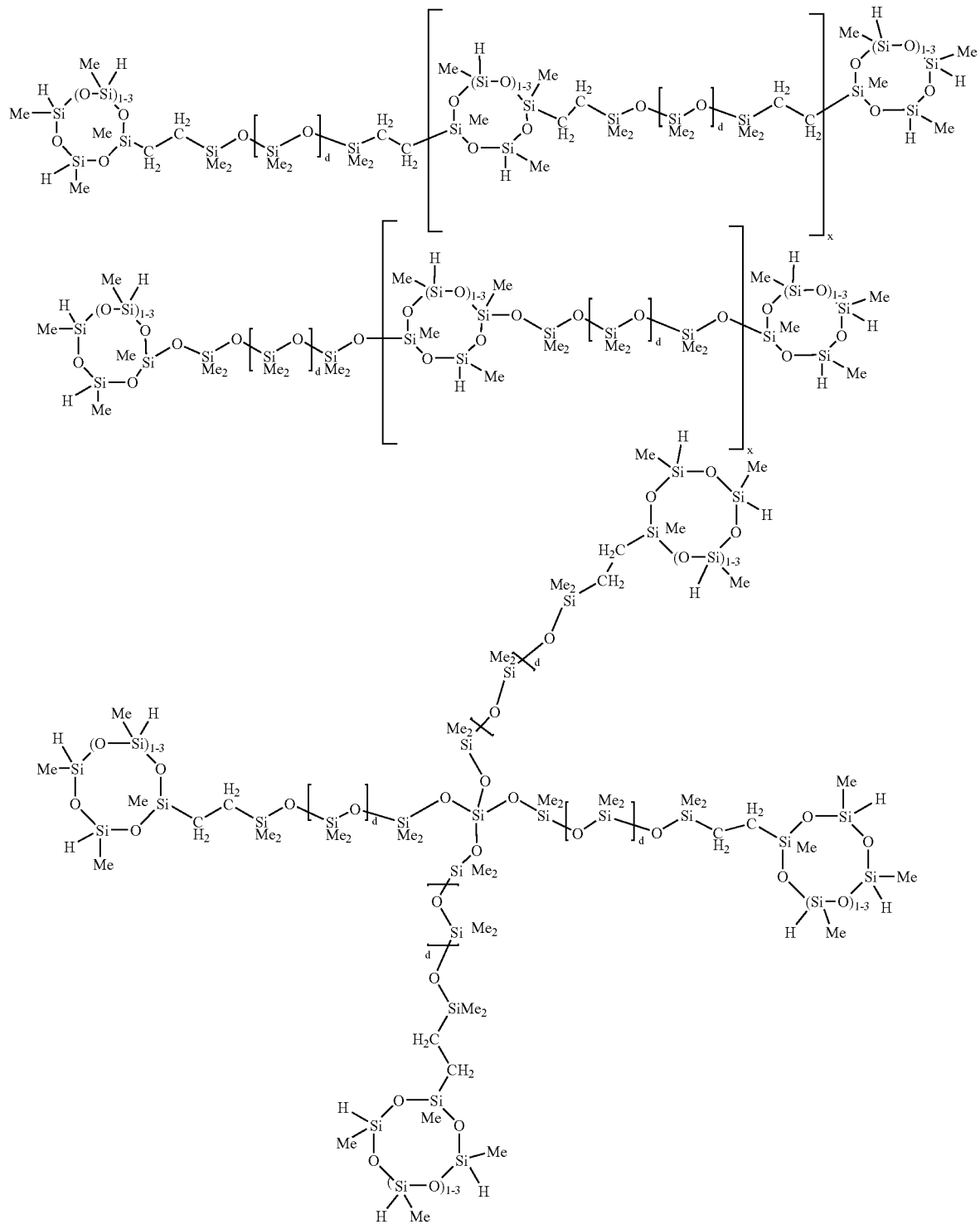

-continued
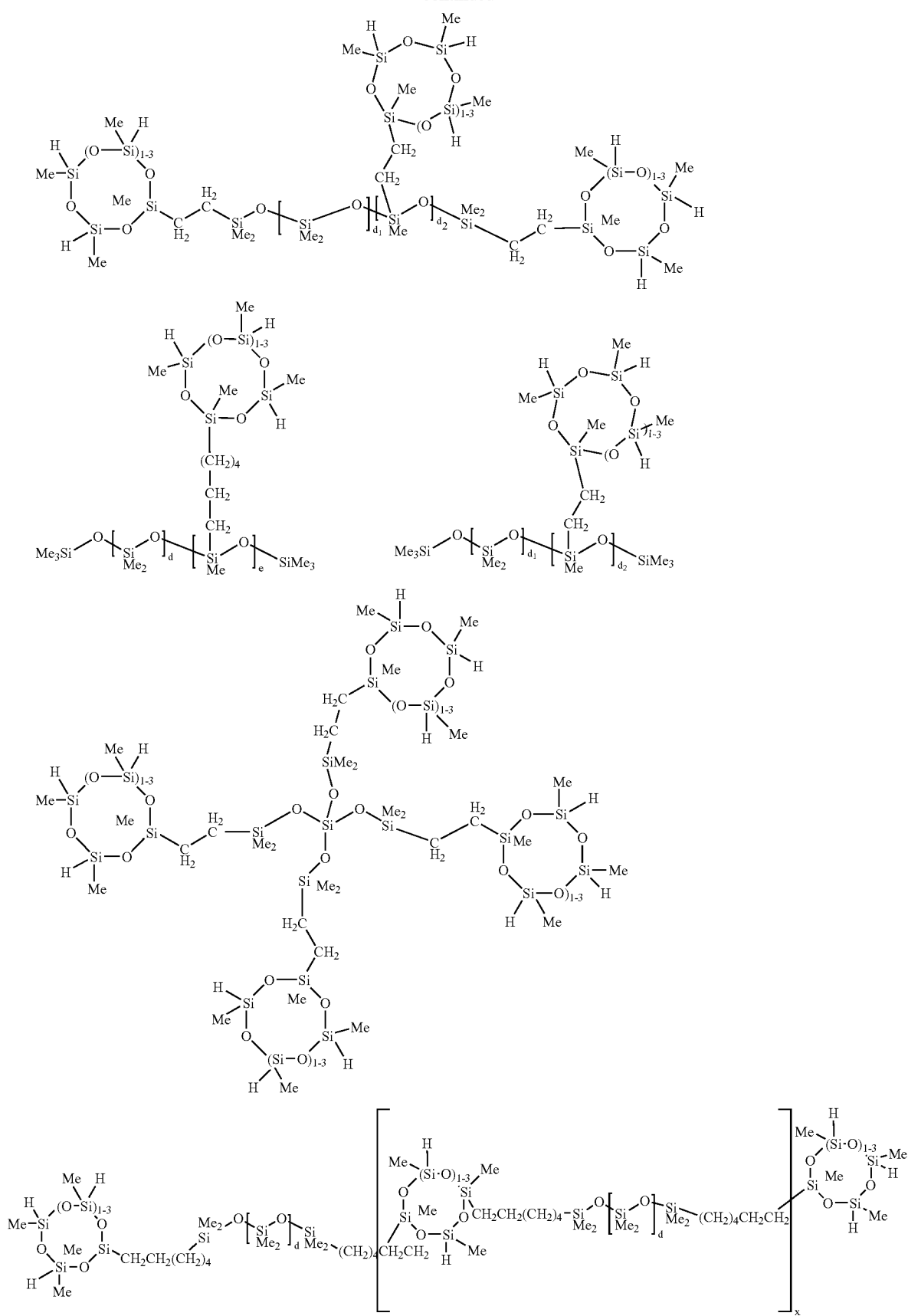

-continued
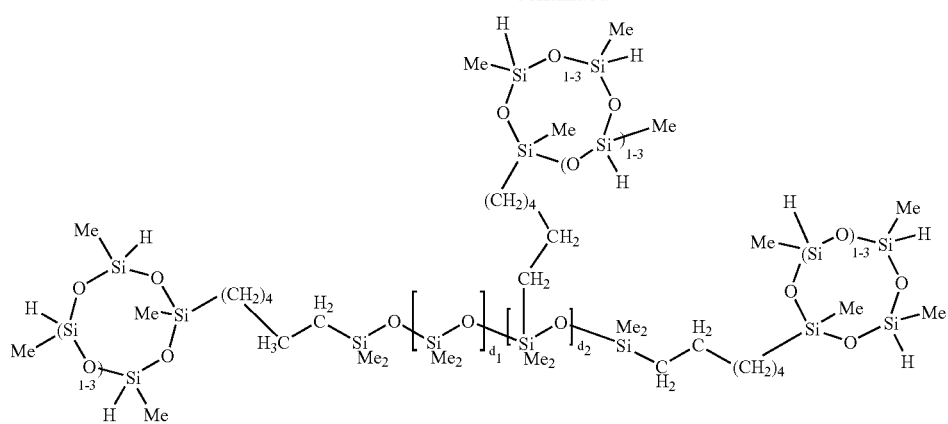
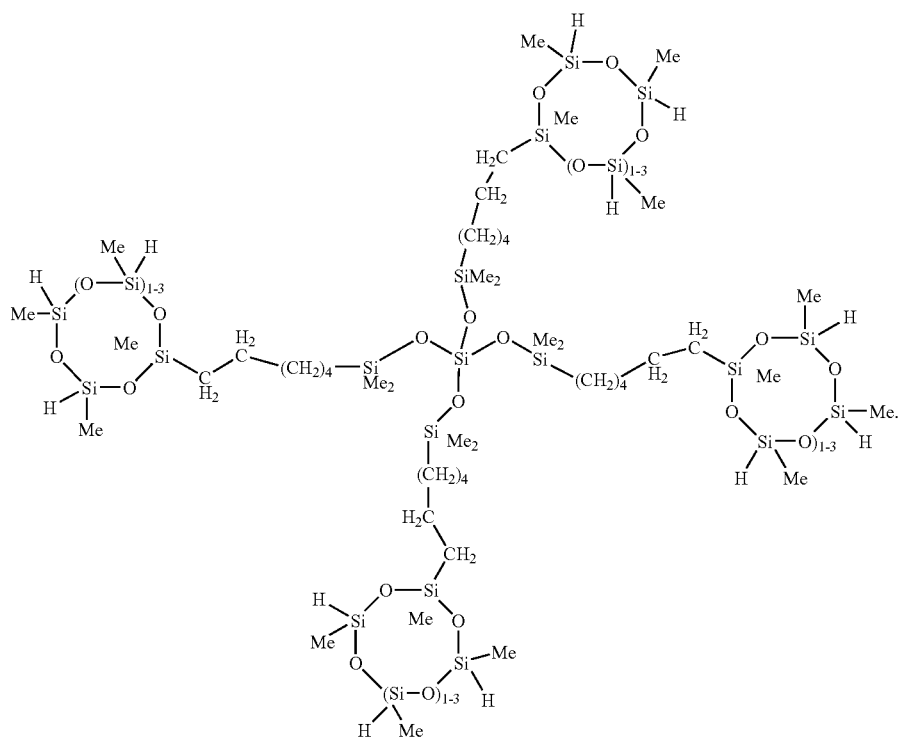

5. A silicon-bonded hydrogen containing branched polymer made by the method of claim 4.

6. A composition comprising the silicon-bonded hydrogen containing branched polymer of claim 5, a Si-alkenyl crosslinker, a platinum-group containing catalyst, and an inhibitor.

7. The method of claim 1 where the organohydrogensilicon compound is described by the structure below where Me is methyl, d is an average of 8, and x is an integer from 1 to 15.

from step (1) with (iv) at least one material having at least one aliphatic unsaturation to form a branched polymer.

11. A branched polymer made by the method of claim 10.

12. A silicon-bonded hydrogen containing branched polymer made by the method of claim 1.

13. A composition comprising the silicon-bonded hydrogen containing branched polymer of claim 12.

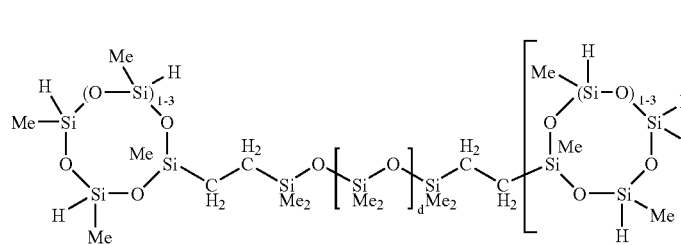

8. The method of claim 1 where R' is independently chosen from alkyl, fluoroalkyl, or alkenyl, component (ii) is added in amounts from 3 to 1000 parts by weight based on 100 parts by weight of component (i) and component (iii) is added in amounts from 0 to 1000 parts by weight.

9. The method of claim 1 where component (i) is the reaction product obtained by mixing in the presence of a platinum group metal-containing catalyst at least one organohydrogensilicon compound containing at least one silicon-bonded hydrogen atom per molecule and at least one compound having at least one aliphatic unsaturation.

10. The method of claim 1 further comprising (2) mixing in the presence of a platinum group metal-containing catalyst, the silicon-bonded hydrogen containing branched polymers 14. A composition comprising the silicon-bonded hydrogen containing branched polymer of claim 12, a Si-alkenyl crosslinker, a platinum-group containing catalyst, and an inhibitor.

15. The method of claim 1 where the acidic ring opening polymerization catalyst is selected from triflic acid and acid ion exchange resins.

16. The method of claim 1 wherein the amount of the acidic ring opening polymerization catalyst is in the range of 10 parts per million to 2 parts by weight based on the total weight percent solids in the composition.

17. The method of claim 1 wherein the polymerization is carried out in the presence of a solvent.

18. The method of claim 1 wherein component (iii) is added in amounts from 100 to 1000 parts by weight.

19. A silicon-bonded hydrogen containing branched polymer made by the method of claim 18.

20. A composition comprising the silicon-bonded hydrogen containing branched polymer of claim 19, a Si-alkenyl crosslinker, a platinum-group containing catalyst, and an inhibitor.

* * * * *